(12) United States Patent
Carroll

(10) Patent No.: US 7,045,505 B2
(45) Date of Patent: May 16, 2006

(54) METHODS OF USING 69039, A NOVEL HUMAN NA/CA EXCHANGER FAMILY MEMBER

(75) Inventor: Joseph M. Carroll, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 589 days.

(21) Appl. No.: 10/256,537

(22) Filed: Sep. 27, 2002

(65) Prior Publication Data

US 2003/0162196 A1  Aug. 28, 2003

Related U.S. Application Data

(60) Provisional application No. 60/325,737, filed on Sep. 28, 2001.

(51) Int. Cl.
*A61K 38/00* (2006.01)
(52) U.S. Cl. ..................................................... 514/12
(58) Field of Classification Search ............... 530/350; 514/12
See application file for complete search history.

(56) References Cited

FOREIGN PATENT DOCUMENTS

| | | |
|---|---|---|
| WO | WO 01/09161 A1 | 2/2001 |
| WO | WO 01/83744 A2 * | 11/2001 |
| WO | WO 01/837744 A3 | 11/2001 |
| WO | WO 02/33086 A2 | 4/2002 |
| WO | WO 02/046415 A2 | 6/2002 |
| WO | WO 02/059316 A2 | 8/2002 |
| WO | WO 02/081625 A2 | 10/2002 |

OTHER PUBLICATIONS

Gabellini, Nadia, "A polymorphic GT repeat from the human cardiac $Na^+Ca^{2+}$ exchanger intron 2 activates splicing," Eur. J. Biochem, 268:1076-1083, 2001.

Kraev, et al., "The Organization of the Human Gene NCX1 Encoding the Sodium-Calcium Exchanger," Genomics, 37:105-112, 1996.

Kraev, et al., "*Homo sapiens* partial SCL8A3 gene for solute carrier family 8 (sodium/calcium exchanger), member 3 (SCL8A3), exon 2," Nov. 12, 2000 (sequence) GenBank [online] Bethesda, MD, USA: National Center for Biotechnology Information [retrieved on Jun. 5, 2005]. Retrieved from the Internet: URL: http://www.ncbi.nlm.nih.gov/>. GenBank Accession No. X93017.

Heilig, et al., "Human chromosome 14 DNA sequence BAC R-486013 of library RPCI-11 from chromosome 14 of *Homo sapiens* (Human), complete sequence," Jul. 10, 2001 (sequence) GenBank [online] Bethesda, MD USA: National Center for Biotechnology Information [retrieved on Jun. 5, 2005]. Retrieved from the Internet: URL: http:www.ncbi/nlm.nih.gov/>. GenBank Accession No. AL160191.

Gabellini, N., "*Homo sapiens* mRNA for sodium/calcium exchanger, SCL8A3, alternative splice form B (SCL8A3 gene)," Jun. 6, 2001 (sequence) GenBank [online] Bethesda, MD, USA: National Center for Biotechnology Information [retrieved on Jun. 5, 2005]. Retrieved from the Internet: URL: http:www.ncbi.nlm.nih.gov/>. GenBank Accession No. AJ304853.

Gabellini, N., "*Homo sapiens* mRNA for sodium/calcium exchanger, SCL8A3, alternative splice form A (SCL8A3 gene)," Jun. 6, 2001 (sequence) GenBank [online] Bethesda, MD, USA: National Center for Biotechnology Information [retrieved on Jun. 5, 2005]. Retrieved from the Internet: URL: http:www.ncbi.nlm.nih.gov/>. GenBank Accession No. AJ304852.

Bortoluzzi, S., *Homo sapiens* mRNA for Sodium/Calcium Exchanger, SCL8A3, Alternative Splice Form B (SCL8A3 Gene), Jun. 6, 2001 (sequence) GenBank [online] Bethesda, MD, USA: National Center for Biotechnology Information [retrieved on Aug. 7, 2003]. Retrieved from the Internet: URL: http://www.ncbi.nim.nih.gov/>. GenBank Accession No. AJ304853.

* cited by examiner

*Primary Examiner*—Robert A. Wax
*Assistant Examiner*—Agnes Rooke
(74) Attorney, Agent, or Firm—Millennium Pharmaceuticals, Inc.

(57) ABSTRACT

Isolated nucleic acids molecules, designated 69039 nucleic acid molecules, which encode novel $Na^+/Ca^{2+}$ exchanger members, are disclosed. The invention also provides antisense nucleic acid molecules, recombinant expression vectors containing 69039 nucleic acid molecules, host cells into which the expression vectors have been introduced, and nonhuman transgenic animals in which a 69039 gene has been introduced or disrupted. Isolated 69039 proteins, fusion proteins, antigenic peptides and anti-69039 antibodies are also disclosed. The invention further provides methods of treating, preventing and diagnosing hematopoietic and neurological disorders.

14 Claims, 7 Drawing Sheets

```
Na_Ca Ex: domain 1 of 1, from 110 to 257: score 121.9, E = 1.2e-32
              *->ilivlgadlfVdgasaiaevlgisesviGlTlvAlGTSlPElfaSli
                 ++      +g +   +++   ++e+v +lTl+AlG S+PE++ Sli
     69039  110    ---REVTIKKPNGETSTTTIRVWNETVSNLTLMALGSSAPEILLSLI 153 aalkgqf.qadiAiGnviGSNifNillglGiasliaplyhkakgesfiVd
              +++++f ++d+++++++GS++fN+++++Gi+   ++p ++++k+++++V+
     69039  154 EVCGHGFiAGDLGPSTIVGSAAFNMFIIIGICVYVIPDGETRKIKHLRVF 203 pislrrdvlflllvllilivflllgrsligrgdgvllilyilyltflvf
              i+ +++++++++  +il+vf +   +++ +++    ++l+++ +++l+++v+
     69039  204 FITAAWSIFAYIWLYMILAVFSP--GVVQVWEGLLTLFFFPVCVLLAWVA 251 sillev<-*    (SEQ ID NO:4)
              +++l++
     69039  252 DKRLLF     257
```

Figure 2

```
NIbeta_1: domain 1 of 2, from 385 to 485: score 152.3, E = 8.6e-42
              *->atvtilDddhagtvgFeqphytVsEsdGevevtVvRtggtargtvvV
                 + t+ ++d +++v+F++   y+++E++G v +tVvR+gg+ ++t +V
      69039 385   EVHTDEPEDFISKVFFDPCSYQCLENCGAVLLTVVRKGGDMSKTMYV 431 pyrTedGTAtaGgsDYepvdIeGtLtFepgegtekeIrikiidDdiyEer
                 +y+TedG+A+aG +DYe +   eGt++ +pge t+ke++++iidDdi+Ee
      69039 432 DYKTEDGSANAG-ADYEFT--EGTVVLKPGE-TQKEFSVGIIDDDIFEE- 476 dEtFyvrLs<-*     (SEQ ID NO:5)
                 dE+F+vrLs
      69039 477 DEHFFVRLS    485

NIbeta_1: domain 2 of 2, from 519 to 594: score 73.5, E = 4.6e-18
              *->atvtilDddhagtvgFeqphytVsEsdGevevtVvRtggtargtvvV
                 atvtilDddhag++ Fe   +++VsEs G++ev+V+Rt+g argtv+V
      69039 519   ATVTILDDDHAGIFTFECDTIHVSESIGVMEVKVLRTSG-ARGTVIV 564 pyrTedGTAtaGgsDYepvdIeGtLtFepgegtekeIrikiidDdiyEer
                 p+rT++GTA++Gg D+e++    G+L+F+++e
      69039 565 PFRTVEGTAKGGGEDFEDT--YGELEFKNDE------------------ 593 dEtFyvrLs<-*     (SEQ ID NO:5)
                      +
      69039 594 --------T     594
```

Figure 3

SEQUENCE LISTING

<160> NUMBER OF SEQ ID NOS: 5

<210> SEQ ID NO 1
<211> LENGTH: 2534
<212> TYPE: DNA
<213> ORGANISM: Homo sapien

<400> SEQUENCE: 1

```
ccagtttggg agacaggact tgaaggctat tgctgcattt ccatccccag tattcccagc     60
tatttcaagc catttttcaa cggagtctcc accagatggt ttggaggaca gagcagctat    120
ttgtgcctcc cattgacatc tatttttcca agtgagagac tgccccatat gttagtgcaa    180
tatgtcactg gaggtgaagc atcagttgta ttggtgggaa cctgccgttt gctgtcccct    240
ttttcctcat gccttttcct gcctctctga tcttttctag gtctctggcc tatcaggagg    300
acaactggtg ctgcaataga agccagtggc taagtctcgt gtatggcgtg gttaaggttg    360
cagcctctca cctctgcctt cctccatttt gggctggtta cctttgtgct cttcctgaat    420
ggtcttcgag cagaggctgg tggctcaggg gacgtgccaa gcacagggca gaacaatgag    480
tcctgttcag ggtcatcgga ctgcaaggag ggtgtcatcc tgccaatctg gtacccggag    540 aaccctttccc ttggggacaa gattgccagg gtcattgtct attttgtggc cctgatatac    600
atgttccttg gggtgtccat cattgctgac cgcttcatgg catctattga agtcatcacc    660
tctcaagaga gggaggtgac aattaagaaa cccaatggaa aaaccagcac aaccactatt    720
cgggtctgga atgaaactgt ctccaacctg acccttatgg ccctgggttc ctctgctcct    780
gagatactcc tctctttaat tgaggtgtgt ggtcatgggt tcattgctgg tgatctggga    840
ccttctacca ttgtagggag tgcagccttc aacatgttca tcatcattgg catctgtgtc    900
tacgtgatcc cagacggaga gactcgcaag atcaagcatc tacgagtctt cttcatcacc    960
```

-continued

```
gctgcttgga gtatctttgc ctacatctgg ctctatatga ttctggcagt cttctcccct    1020
ggtgtggtcc aggtttggga aggcctcctc actctcttct tctttccagt gtgtgtcctt    1080
ctggcctggg tggcagataa acgactgctc ttctacaaat acatgcacaa aaagtaccgc    1140
acagacaaac accgaggaat tatcatagag acagaggtg accaccctaa gggcattgag     1200
atggatggga aaatgatgaa ttcccatttt ctagatggga acctggtgcc cctggaaggg    1260
aaggaagtgg atgagtcccg cagagagatg atccggattc tcaaggatct gaagcaaaaa    1320
cacccagaga aggacttaga tcagctggtg gagatggcca attactatgc tctttcccac    1380
caacagaaga gccgcgcctt ctaccgtatc caagccactc gtatgatgac tggtgcaggc    1440
aatatcctga gaaacatgc agcagaacaa gccaagaagg cctccagcat gagcgaggtg      1500
cacaccgatg agcctgagga ctttatttcc aaggtcttct ttgacccatg ttcttaccag    1560
tgcctggaga actgtggggc tgtactcctg acagtggtga ggaaggggg agacatgtca     1620 aagaccatgt atgtggacta caaaacagag gatggttctg ccaatgcagg ggctgactat    1680
gagttcacag agggcacggt ggttctgaag ccaggagaga cccagaagga gttctccgtg    1740
ggcataattg atgacgacat ttttgaggag gatgaacact tctttgtaag gttgagcaat    1800
gtccgcatag aggaggagca gccagaggag gggatgcctc cagcaatatt caacagtctt    1860
cccttgcctc gggctgtcct agcctcccct tgtgtggcca cagttaccat cttggatgat    1920
gaccatgcag gcatcttcac ttttgaatgt gatactattc atgtcagtga gagtattggt    1980 gttatgagg tcaaggttct gcggacatca ggtgcccggg gtacagtcat cgtccccttt    2040
aggacagtag aagggacagc caagggtggc ggtgaggact ttgaagacac atatggggag    2100
ttggaattca gaatgatga aactgtgtaa gtaaccttcc tgtattctgc ccctccctga    2160
ccccatcttt tgccatctct ttctgtcttt ctgtactgca ctttacaaca tttccttgtg    2220
tttgtgttaa tgtcaaactt tggttccatc acaggtatgc aggatcagca gacaccactg    2280
gacaggttct gcttccaaac tcttcttcag ttttctcact ttaaattgtt tctgggcaag    2340
gaatcctgtg acaagagcta aggacacaaa acatttttctt ctctgaaaca caaaatgata    2400
gctggtggag ctgtgggatg acagaagttt tgtgatatca gattttggag aattcttgtg    2460
actaagaagg actagagaac tgcttgggcc tcttcttcct cccttcctca tatgaagggt    2520
atctatgagc tttg                                                      2534
```

<210> SEQ ID NO 2
<211> LENGTH: 595
<212> TYPE: PRT
<213> ORGANISM: Homo sapien

<400> SEQUENCE: 2

```
Met Ala Trp Leu Arg Leu Gln Pro Leu Thr Ser Ala Phe Leu His Phe
  1               5                  10                  15

Gly Leu Val Thr Phe Val Leu Phe Leu Asn Gly Leu Arg Ala Glu Ala
                 20                  25                  30

Gly Gly Ser Gly Asp Val Pro Ser Thr Gly Gln Asn Asn Glu Ser Cys
             35                  40                  45

Ser Gly Ser Ser Asp Cys Lys Glu Gly Val Ile Leu Pro Ile Trp Tyr
         50                  55                  60

Pro Glu Asn Pro Ser Leu Gly Asp Lys Ile Ala Arg Val Ile Val Tyr
 65                  70                  75                  80

Phe Val Ala Leu Ile Tyr Met Phe Leu Gly Val Ser Ile Ile Ala Asp
```

-continued

```
                 85                  90                  95
Arg Phe Met Ala Ser Ile Glu Val Ile Thr Ser Gln Glu Arg Glu Val
                100                 105                 110
Thr Ile Lys Lys Pro Asn Gly Glu Thr Ser Thr Thr Thr Ile Arg Val
                115                 120                 125
Trp Asn Glu Thr Val Ser Asn Leu Thr Leu Met Ala Leu Gly Ser Ser
                130                 135                 140
Ala Pro Glu Ile Leu Leu Ser Leu Ile Glu Val Cys Gly His Gly Phe
145                 150                 155                 160
Ile Ala Gly Asp Leu Gly Pro Ser Thr Ile Val Gly Ser Ala Ala Phe
                165                 170                 175
Asn Met Phe Ile Ile Gly Ile Cys Val Tyr Val Ile Pro Asp Gly
                180                 185                 190
Glu Thr Arg Lys Ile Lys His Leu Arg Val Phe Phe Ile Thr Ala Ala
                195                 200                 205
Trp Ser Ile Phe Ala Tyr Ile Trp Leu Tyr Met Ile Leu Ala Val Phe
                210                 215                 220
Ser Pro Gly Val Val Gln Val Trp Glu Gly Leu Leu Thr Leu Phe Phe
225                 230                 235                 240
Phe Pro Val Cys Val Leu Leu Ala Trp Val Ala Asp Lys Arg Leu Leu
                245                 250                 255
Phe Tyr Lys Tyr Met His Lys Lys Tyr Arg Thr Asp Lys His Arg Gly
                260                 265                 270
Ile Ile Ile Glu Thr Glu Gly Asp His Pro Lys Gly Ile Glu Met Asp
                275                 280                 285
Gly Lys Met Met Asn Ser His Phe Leu Asp Gly Asn Leu Val Pro Leu
290                 295                 300
Glu Gly Lys Glu Val Asp Glu Ser Arg Arg Glu Met Ile Arg Ile Leu
305                 310                 315                 320
Lys Asp Leu Lys Gln Lys His Pro Glu Lys Asp Leu Asp Gln Leu Val
                325                 330                 335
Glu Met Ala Asn Tyr Tyr Ala Leu Ser His Gln Gln Lys Ser Arg Ala
                340                 345                 350
Phe Tyr Arg Ile Gln Ala Thr Arg Met Met Thr Gly Ala Gly Asn Ile
                355                 360                 365
Leu Lys Lys His Ala Ala Glu Gln Ala Lys Lys Ala Ser Ser Met Ser
                370                 375                 380
Glu Val His Thr Asp Glu Pro Glu Asp Phe Ile Ser Lys Val Phe Phe
385                 390                 395                 400
Asp Pro Cys Ser Tyr Gln Cys Leu Glu Asn Cys Gly Ala Val Leu Leu
                405                 410                 415
Thr Val Arg Lys Gly Gly Asp Met Ser Lys Thr Met Tyr Val Asp
                420                 425                 430
Tyr Lys Thr Glu Asp Gly Ser Ala Asn Ala Gly Ala Asp Tyr Glu Phe
                435                 440                 445
Thr Glu Gly Thr Val Val Leu Lys Pro Gly Glu Thr Gln Lys Glu Phe
                450                 455                 460
Ser Val Gly Ile Ile Asp Asp Asp Ile Phe Glu Glu Asp Glu His Phe
465                 470                 475                 480
Phe Val Arg Leu Ser Asn Val Arg Ile Glu Glu Gln Pro Glu Glu
                485                 490                 495
Gly Met Pro Pro Ala Ile Phe Asn Ser Leu Pro Leu Pro Arg Ala Val
                500                 505                 510
```

```
Leu Ala Ser Pro Cys Val Ala Thr Val Thr Ile Leu Asp Asp His
        515                 520                 525

Ala Gly Ile Phe Thr Phe Glu Cys Asp Thr Ile His Val Ser Glu Ser
        530                 535                 540

Ile Gly Val Met Glu Val Lys Val Leu Arg Thr Ser Gly Ala Arg Gly
545                 550                 555                 560

Thr Val Ile Val Pro Phe Arg Thr Val Glu Gly Thr Ala Lys Gly Gly
                565                 570                 575

Gly Glu Asp Phe Glu Asp Thr Tyr Gly Glu Leu Glu Phe Lys Asn Asp
            580                 585                 590

Glu Thr Val
        595

<210> SEQ ID NO 3
<211> LENGTH: 2534
<212> TYPE: DNA
<213> ORGANISM: Homo sapien
<220> FEATURE:
<221> NAME/KEY: CDS
<222> LOCATION: (343)...(2130)

<400> SEQUENCE: 3
ccagtttggg agacaggact tgaaggctat tgctgcattt ccatccccag tattcccagc      60
tatttcaagc cattttttcaa cggagtctcc accagatggt ttggaggaca gagcagctat   120
ttgtgcctcc cattgacatc tattttttcca agtgagagac tgccccatat gttagtgcaa   180
tatgtcactg gaggtgaagc atcagttgta ttggtgggaa cctgccgttt gctgtcccct   240
ttttcctcat gccttttcct gcctctctga tcttttctag gtctctggcc tatcaggagg   300
acaactggtg ctgcaataga agccagtggc taagtctcgt gt atg gcg tgg tta      354
                                              Met Ala Trp Leu
                                                    1 agg ttg cag cct ctc acc tct gcc ttc ctc cat ttt ggg ctg gtt acc      402
Arg Leu Gln Pro Leu Thr Ser Ala Phe Leu His Phe Gly Leu Val Thr
  5                  10                  15                  20 ttt gtg ctc ttc ctg aat ggt ctt cga gca gag gct ggt ggc tca ggg      450
Phe Val Leu Phe Leu Asn Gly Leu Arg Ala Glu Ala Gly Gly Ser Gly
                 25                  30                  35 gac gtg cca agc aca ggg cag aac aat gag tcc tgt tca ggg tca tcg      498
Asp Val Pro Ser Thr Gly Gln Asn Asn Glu Ser Cys Ser Gly Ser Ser
             40                  45                  50 gac tgc aag gag ggt gtc atc ctg cca atc tgg tac ccg gag aac cct      546
Asp Cys Lys Glu Gly Val Ile Leu Pro Ile Trp Tyr Pro Glu Asn Pro
         55                  60                  65 tcc ctt ggg gac aag att gcc agg gtc att gtc tat ttt gtg gcc ctg      594
Ser Leu Gly Asp Lys Ile Ala Arg Val Ile Val Tyr Phe Val Ala Leu
     70                  75                  80 ata tac atg ttc ctt ggg gtg tcc atc att gct gac cgc ttc atg gca      642
Ile Tyr Met Phe Leu Gly Val Ser Ile Ile Ala Asp Arg Phe Met Ala
 85                  90                  95                 100 tct att gaa gtc atc acc tct caa gag agg gag gtg aca att aag aaa      690
Ser Ile Glu Val Ile Thr Ser Gln Glu Arg Glu Val Thr Ile Lys Lys
                105                 110                 115 ccc aat gga gaa acc agc aca acc act att cgg gtc tgg aat gaa act      738
Pro Asn Gly Glu Thr Ser Thr Thr Thr Ile Arg Val Trp Asn Glu Thr
            120                 125                 130 gtc tcc aac ctg acc ctt atg gcc ctg ggt tcc tct gct cct gag ata      786
Val Ser Asn Leu Thr Leu Met Ala Leu Gly Ser Ser Ala Pro Glu Ile
        135                 140                 145
```

-continued

| | |
|---|---|
| ctc ctc tct tta att gag gtg tgt ggt cat ggg ttc att gct ggt gat<br>Leu Leu Ser Leu Ile Glu Val Cys Gly His Gly Phe Ile Ala Gly Asp<br>150                             155                            160 | 834 |
| ctg gga cct tct acc att gta ggg agt gca gcc ttc aac atg ttc atc<br>Leu Gly Pro Ser Thr Ile Val Gly Ser Ala Ala Phe Asn Met Phe Ile<br>165                             170                         175                    180 | 882 |
| atc att ggc atc tgt gtc tac gtg atc cca gac gga gag act cgc aag<br>Ile Ile Gly Ile Cys Val Tyr Val Ile Pro Asp Gly Glu Thr Arg Lys<br>                        185                         190                        195 | 930 |
| atc aag cat cta cga gtc ttc ttc atc acc gct gct tgg agt atc ttt<br>Ile Lys His Leu Arg Val Phe Phe Ile Thr Ala Ala Trp Ser Ile Phe<br>                200                         205                        210 | 978 |
| gcc tac atc tgg ctc tat atg att ctg gca gtc ttc tcc cct ggt gtg<br>Ala Tyr Ile Trp Leu Tyr Met Ile Leu Ala Val Phe Ser Pro Gly Val<br>                      215                         220                        225 | 1026 |
| gtc cag gtt tgg gaa ggc ctc ctc act ctc ttc ttc ttt cca gtg tgt<br>Val Gln Val Trp Glu Gly Leu Leu Thr Leu Phe Phe Phe Pro Val Cys<br>230                             235                         240 | 1074 |
| gtc ctt ctg gcc tgg gtg gca gat aaa cga ctg ctc ttc tac aaa tac<br>Val Leu Leu Ala Trp Val Ala Asp Lys Arg Leu Leu Phe Tyr Lys Tyr<br>245                           250                         255                    260 | 1122 |
| atg cac aaa aag tac cgc aca gac aaa cac cga gga att atc ata gag<br>Met His Lys Lys Tyr Arg Thr Asp Lys His Arg Gly Ile Ile Ile Glu<br>                        265                         270                        275 | 1170 |
| aca gag ggt gac cac cct aag ggc att gag atg gat ggg aaa atg atg<br>Thr Glu Gly Asp His Pro Lys Gly Ile Glu Met Asp Gly Lys Met Met<br>                    280                         285                        290 | 1218 |
| aat tcc cat ttt cta gat ggg aac ctg gtg ccc ctg gaa ggg aag gaa<br>Asn Ser His Phe Leu Asp Gly Asn Leu Val Pro Leu Glu Gly Lys Glu<br>                        295                         300                        305 | 1266 |
| gtg gat gag tcc cgc aga gag atg atc cgg att ctc aag gat ctg aag<br>Val Asp Glu Ser Arg Arg Glu Met Ile Arg Ile Leu Lys Asp Leu Lys<br>310                             315                         320 | 1314 |
| caa aaa cac cca gag aag gac tta gat cag ctg gtg gag atg gcc aat<br>Gln Lys His Pro Glu Lys Asp Leu Asp Gln Leu Val Glu Met Ala Asn<br>325                             330                         335                    340 | 1362 |
| tac tat gct ctt tcc cac caa cag aag agc cgc gcc ttc tac cgt atc<br>Tyr Tyr Ala Leu Ser His Gln Gln Lys Ser Arg Ala Phe Tyr Arg Ile<br>                        345                         350                        355 | 1410 |
| caa gcc act cgt atg atg act ggt gca ggc aat atc ctg aag aaa cat<br>Gln Ala Thr Arg Met Met Thr Gly Ala Gly Asn Ile Leu Lys Lys His<br>                    360                         365                        370 | 1458 |
| gca gca gaa caa gcc aag aag gcc tcc agc atg agc gag gtg cac acc<br>Ala Ala Glu Gln Ala Lys Lys Ala Ser Ser Met Ser Glu Val His Thr<br>                        375                         380                        385 | 1506 |
| gat gag cct gag gac ttt att tcc aag gtc ttc ttt gac cca tgt tct<br>Asp Glu Pro Glu Asp Phe Ile Ser Lys Val Phe Phe Asp Pro Cys Ser<br>390                             395                         400 | 1554 |
| tac cag tgc ctg gag aac tgt ggg gct gta ctc ctg aca gtg gtg agg<br>Tyr Gln Cys Leu Glu Asn Cys Gly Ala Val Leu Leu Thr Val Val Arg<br>405                             410                         415                    420 | 1602 |
| aaa ggg gga gac atg tca aag acc atg tat gtg gac tac aaa aca gag<br>Lys Gly Gly Asp Met Ser Lys Thr Met Tyr Val Asp Tyr Lys Thr Glu<br>                        425                         430                        435 | 1650 |
| gat ggt tct gcc aat gca ggg gct gac tat gag ttc aca gag ggc acg<br>Asp Gly Ser Ala Asn Ala Gly Ala Asp Tyr Glu Phe Thr Glu Gly Thr<br>                    440                         445                        450 | 1698 |
| gtg gtt ctg aag cca gga gag acc cag aag gag ttc tcc gtg ggc ata<br>Val Val Leu Lys Pro Gly Glu Thr Gln Lys Glu Phe Ser Val Gly Ile | 1746 |

```
                  455                 460                 465
att gat gac gac att ttt gag gag gat gaa cac ttc ttt gta agg ttg      1794
Ile Asp Asp Asp Ile Phe Glu Glu Asp Glu His Phe Phe Val Arg Leu
        470                 475                 480 agc aat gtc cgc ata gag gag gag cag cca gag gag ggg atg cct cca      1842
Ser Asn Val Arg Ile Glu Glu Glu Gln Pro Glu Glu Gly Met Pro Pro
485                 490                 495                 500 gca ata ttc aac agt ctt ccc ttg cct cgg gct gtc cta gcc tcc cct      1890
Ala Ile Phe Asn Ser Leu Pro Leu Pro Arg Ala Val Leu Ala Ser Pro
                505                 510                 515 tgt gtg gcc aca gtt acc atc ttg gat gat gac cat gca ggc atc ttc      1938
Cys Val Ala Thr Val Thr Ile Leu Asp Asp Asp His Ala Gly Ile Phe
            520                 525                 530 act ttt gaa tgt gat act att cat gtc agt gag agt att ggt gtt atg      1986
Thr Phe Glu Cys Asp Thr Ile His Val Ser Glu Ser Ile Gly Val Met
        535                 540                 545 gag gtc aag gtt ctg cgg aca tca ggt gcc cgg ggt aca gtc atc gtc      2034
Glu Val Lys Val Leu Arg Thr Ser Gly Ala Arg Gly Thr Val Ile Val
    550                 555                 560 ccc ttt agg aca gta gaa ggg aca gcc aag ggt ggc ggt gag gac ttt      2082
Pro Phe Arg Thr Val Glu Gly Thr Ala Lys Gly Gly Gly Glu Asp Phe
565                 570                 575                 580 gaa gac aca tat ggg gag ttg gaa ttc aag aat gat gaa act gtg taa      2130
Glu Asp Thr Tyr Gly Glu Leu Glu Phe Lys Asn Asp Glu Thr Val  *
                585                 590                 595 gtaaccttcc tgtattctgc ccctccctga ccccatcttt tgccatctct ttctgtcttt   2190
ctgtactgca ctttacaaca tttccttgtg tttgtgttaa tgtcaaactt tggttccatc   2250
acaggtatgc aggatcagca gacaccactg gacaggttct gcttccaaac tcttcttcag   2310
ttttctcact ttaaattgtt tctgggcaag gaatcctgtg acaagagcta aggacacaaa   2370
acattttctt ctctgaaaca caaaatgata gctggtggag ctgtgggatg acagaagttt   2430
tgtgatatca gattttggag aattcttgtg actaagaagg actagagaac tgcttgggcc   2490
tcttcttcct cccttcctca tatgaagggt atctatgagc tttg                   2534
```

<210> SEQ ID NO 4
<211> LENGTH: 152
<212> TYPE: PRT
<213> ORGANISM: Homo sapien

<400> SEQUENCE: 4

```
Ile Leu Ile Val Leu Gly Ala Asp Leu Phe Val Asp Gly Ala Ser Ala
1               5                   10                  15

Ile Ala Glu Val Leu Gly Ile Ser Glu Ser Val Ile Gly Leu Thr Leu
            20                  25                  30

Val Ala Leu Gly Thr Ser Leu Pro Glu Leu Phe Ala Ser Leu Ile Ala
        35                  40                  45

Ala Leu Lys Gly Gln Phe Gln Ala Asp Ile Ala Ile Gly Asn Val Ile
    50                  55                  60

Gly Ser Asn Ile Phe Asn Ile Leu Gly Leu Gly Ile Ala Ser Leu
65                  70                  75                  80

Ile Ala Pro Leu Tyr His Lys Ala Lys Gly Glu Ser Phe Ile Val Asp
                85                  90                  95

Pro Ile Ser Leu Arg Arg Asp Val Leu Phe Leu Leu Val Leu Leu
            100                 105                 110

Ile Leu Ile Val Phe Leu Leu Gly Arg Ser Leu Ile Gly Arg Gly
        115                 120                 125
```

-continued

```
Asp Gly Val Leu Leu Leu Ile Leu Tyr Ile Leu Tyr Leu Thr Phe Leu
    130                 135                 140

Val Phe Ser Ile Leu Leu Glu Val
145                 150

<210> SEQ ID NO 5
<211> LENGTH: 106
<212> TYPE: PRT
<213> ORGANISM: Homo sapien

<400> SEQUENCE: 5

Ala Thr Val Thr Ile Leu Asp Asp His Ala Gly Thr Val Gly Phe
  1               5                  10                  15

Glu Gln Pro His Tyr Thr Val Ser Glu Ser Asp Gly Glu Val Glu Val
                 20                  25                  30

Thr Val Val Arg Thr Gly Gly Thr Ala Arg Gly Thr Val Val Val Pro
                 35                  40                  45

Tyr Arg Thr Glu Asp Gly Thr Ala Thr Ala Gly Gly Ser Asp Tyr Glu
     50                  55                  60

Pro Val Asp Ile Glu Gly Thr Leu Thr Phe Glu Pro Gly Glu Gly Thr
 65                  70                  75                  80

Glu Lys Glu Ile Arg Ile Lys Ile Ile Asp Asp Asp Ile Tyr Glu Glu
                 85                  90                  95

Arg Asp Glu Thr Phe Tyr Val Arg Leu Ser
                100                 105
```

METHODS OF USING 69039, A NOVEL HUMAN NA/CA EXCHANGER FAMILY MEMBER

CROSS REFERENCE TO RELATED APPLICATIONS

This application claims the benefit of U.S. Provisional Application No. 60/325737, filed Sep. 28, 2001 the contents of which are incorporated herein by this reference.

BACKGROUND OF THE INVENTION

Cytosolic $Ca^{2+}$ plays a key role in intracellular signaling, and in particular, in regulating proliferation/differentiation in a number of cell types. In many instances, as exemplified by cardiac muscle contraction and the transient release of neurotransmitter substances, the elevated cytosolic free $Ca^{2+}$ concentration may be required for only brief periods of time. The $Ca^{2+}$ must then be rapidly removed from the cytosol by a means such as a $Na^+/Ca^{2+}$ exchanger, a $Ca^{2+}$-selective ion channel, or an ATP-driven $Ca^{2+}$ pump.

The $Na^+/Ca^{2+}$ exchanger, an ion transport protein, is expressed in the plasma membrane of all animal cells (for reviews, see, e.g., Blaustein & Lederer (1999). *Physiol. Rev* 79: 763–854). It extrudes $Ca^{2+}$ in parallel with the plasma membrane ATP-driven $Ca^{2+}$ pump. As a reversible transporter, it also mediates $Ca^{2+}$ entry in parallel with various ion channels. The energy for net $Ca^{2+}$ transport by the $Na^+/Ca^{2+}$ exchanger and its direction depend on the $Na^+$, $Ca^{2+}$, and $K^+$ gradients across the plasma membrane, the membrane potential, and the transport stoichiometry. In most cells, three $Na^+$ are exchanged for one $Ca^{2+}$. In vertebrate photoreceptors, some neurons, and certain other cells, $K^+$ is transported in the same direction as $Ca^{2+}$, with a coupling ratio of four $Na^+$ to one $Ca^{2+}$ plus one $K^+$. The exchanger kinetics are affected by nontransported $Ca^{2+}$, $Na^+$, protons, ATP, and diverse other modulators. Five genes that code for the exchangers have been identified in mammals: three in the $Na^+/Ca^{2+}$ exchanger family (NCX1, NCX2, and NCX3) and two in the $Na^+/Ca^{2+}$ plus $K^+$ family (NCKX1 and NCKX2). See, for example, Nicoll et al. (1990) *Science* 250: 562–565; Li et al. (1994) *J. Biol. Chem.* 269: 17434–17439; and Nicoll et al. (1996) *J. Biol. Chem.* 271: 24914–24921.

At the structural level, all three $Na^+/Ca^{2+}$ exchangers are modeled to have 11 transmembrane segments with a large intracellular loop between the fifth and sixth transmembrane segments. See, e.g., Hilgemann et al. (1991) *Nature* 352: 715–718. At the functional level, only NCX1 has been well characterized. Mutagenesis experiments indicate that specific regions of the transmembrane segments are critical in the ion transport process (Nicoll et al. (1996) *J. Biol. Chem.* 271: 13385–13391). The large intracellular loop of NCX1 is primarily involved in various regulatory properties, such as intracellular $Na^+$-dependent inactivation and $Ca^{2+}$-dependent regulation. See, e.g., Hilgemann (1990) *Nature* 344: 242–245. In addition, each of the NCX exchangers has distinctive putative phosphorylation sites, although roles for each of these sites have not been elucidated. NCX1 of rat smooth and cardiac muscle is phosphorylated by protein kinase C, with a resultant modest stimulation of transport activity (Iwamoto et al. (1996) *J. Biol. Chem.* 271: 13609–13615). NCX1, NCX2, and NCX3 have similar consensus sites for tyrosine phosphorylation.

SUMMARY OF THE INVENTION

Nucleotide and corresponding amino acid sequences for a Na/Ca exchanger family member, referred to herein as "69039" are disclosed. The nucleotide sequence of a cDNA encoding 69039 is shown in SEQ ID NO:1, and the amino acid sequence of a 69039 polypeptide is shown in SEQ ID NO:2. In addition, the nucleotide sequences of the coding region are depicted in SEQ ID NO:3. 69039 protein is a member of a family of ion transporters known as $Na^+/Ca^{2+}$ exchangers. Applicants have shown expression of 69039 mRNA in human hematopoietic cells, e.g., CD34-expressing progenitor cells, as well as neural tissues, e.g., brain cortex and hypothalamus. Accordingly, modulators of 69039 polypeptide activity or expression may be used to treat or prevent hematopoietic and neurological disorders.

Accordingly, in one aspect, the invention features a nucleic acid molecule that encodes a 69039 protein or polypeptide, e.g., a biologically active portion of the 69039 protein. In a preferred embodiment the isolated nucleic acid molecule encodes a polypeptide having the amino acid sequence of SEQ ID NO:2. In other embodiments, the invention provides isolated 69039 nucleic acid molecules having the nucleotide sequence shown in SEQ ID NO:1, SEQ ID NO:3. In still other embodiments, the invention provides nucleic acid molecules that are substantially identical (e.g., naturally occurring allelic variants) to the nucleotide sequence shown in SEQ ID NO:1, SEQ ID NO:3. In other embodiments, the invention provides a nucleic acid molecule which hybridizes under a stringency condition described herein to a nucleic acid molecule comprising the nucleotide sequence of SEQ ID NO:1, SEQ ID NO:3, wherein the nucleic acid encodes a full length 69039 protein or an active fragment thereof.

In a related aspect, the invention further provides nucleic acid constructs that include a 69039 nucleic acid molecule described herein. In certain embodiments, the nucleic acid molecules of the invention are operatively linked to native or heterologous regulatory sequences. Also included, are vectors and host cells containing the 69039 nucleic acid molecules of the invention e.g., vectors and host cells suitable for producing 69039 nucleic acid molecules and polypeptides.

In another related aspect, the invention provides nucleic acid fragments suitable as primers or hybridization probes for the detection of 69039-encoding nucleic acids.

In still another related aspect, isolated nucleic acid molecules that are antisense to a 69039 encoding nucleic acid molecule are provided.

In another aspect, the invention features, 69039 polypeptides, and biologically active or antigenic fragments thereof that are useful, e.g., as reagents or targets in assays applicable to treatment and diagnosis of 69039-mediated or -related disorders. In another embodiment, the invention provides 69039 polypeptides having a 69039 activity. Preferred polypeptides are 69039 proteins including at least one $Na^+/Ca^{2+}$ exchanger domain, and at least one or two Calx-θ motifs, preferably, having a 69039 activity, e.g., a 69039 activity as described herein.

In other embodiments, the invention provides 69039 polypeptides, e.g., a 69039 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence which hybridizes under a stringency condition described herein to a nucleic acid molecule comprising the nucleotide sequence of SEQ ID NO:1, SEQ ID NO:3, wherein the nucleic acid encodes a full length 69039 protein or an active fragment thereof.

In a related aspect, the invention further provides nucleic acid constructs that include a 69039 nucleic acid molecule described herein.

In a related aspect, the invention provides 69039 polypeptides or fragments operatively linked to non-69039 polypeptides to form fusion proteins.

In another aspect, the invention features antibodies and antigen-binding fragments thereof, that react with, or more preferably specifically bind 69039 polypeptides.

In another aspect, the invention provides methods of screening for compounds that modulate the expression or activity of the 69039 polypeptides or nucleic acids.

In still another aspect, the invention provides a process for modulating 69039-polypeptide or nucleic acid expression or activity, e.g., using the screened compounds. In certain embodiments, the methods involve treatment of conditions or disorders related to decreased activity or expression of the 69039 polypeptides or nucleic acids, such as conditions or disorders involving aberrant cellular proliferation or differentiation of a 69039 expressing cell, e.g., a hematopoietic cell (e.g., an erythroid cell (e.g., an erythrocyte or an erythroblast), a CD34 positive cell, a glycophorin A-expressing cell, a megakaryocyte), or a neural cell, e.g., a cortical or hypothalamic neuronal or glial cell. The condition or disorder may involve increased hematopoietic cell activity or proliferation as in the case of leukemia, e.g., an erythroleukemia; or decreased hematopoietic cell differentiation as in the case of, e.g., an anemia. In other embodiments, the condition or disorder is a neurological disorder.

In still another aspect, the invention features a method of modulating (e.g., enhancing or inhibiting) the proliferation, survival, and/or differentiation of a cell, e.g., a 69039-expressing cell, e.g., a hematopoietic cell (e.g., an erythroid cell, a bone marrow cell such as a CD34 positive cell, a megakaryocyte), or a neural cell, e.g., a cortical or hypothalamic neuronal or glial cell. The method includes contacting the cell with an agent that modulates the activity or expression of a 69039 polypeptide or nucleic acid, in an amount effective to modulate the proliferation and/or differentiation of the cell.

In a preferred embodiment, the 69039 polypeptide has an amino acid sequence identical to, or substantially identical to, SEQ ID NO:2. In other embodiments, the 69039 polypeptide is a fragment of at least 15, 20, 50, 100, 150, or more contiguous amino acids of SEQ ID NO:2.

In a preferred embodiment, the 69039 nucleic acid has a nucleotide sequence identical to, or substantially identical to, SEQ ID NO:1 or 3. In other embodiments, the 69039 nucleic acid is a fragment of at least 50, 100, 150, 200, 250, 300, 350, 400, 450, 500, or more contiguous nucleotides of SEQ ID NO:1 or 3.

In a preferred embodiment, the agent modulates (e.g., increases or decreases) one or more of: proliferation/differentiation of a 69039-expressing cell; intracellular $Ca^{2+}$ concentration; or $Na^+$-dependent inactivation and $Ca^{2+}$-dependent regulation of a 69039 polypeptide; ion, e.g., sodium or calcium, flux across a cell membrane.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 69039 nucleic acid, or any combination thereof.

In a preferred embodiment, the agent is administered in combination with a cytotoxic agent.

In a preferred embodiment, the cell, e.g., the 69039-expressing cell, is a hematopoietic cell, e.g., a myeloid, lymphoid or erythroid cell, or a precursor cell thereof. Examples of such cells include myelocytic cells (polymorphonuclear cells), erythrocytic cells, lymphocytes, monocytes, reticular cells, plasma cells and megakaryocytes, as well as stem cells for the different lineages, and precursors for the committed progenitor cells, for example, precursors of blood cells (e.g., red blood cells, such as erythroblasts), macrophages (monoblasts), platelets (megakaryocytes), polymorphonuclear leucocytes (myeloblasts), and lymphocytes (lymphoblasts).

In a preferred embodiment, the cell, e.g., the 69039-expressing cell, is a bone marrow cell, e.g., a bone marrow CD34-expressing cell. Examples of CD34-expressing cells include immature hematopoietic precursor cells, hematopoietic colony-forming cells in bone marrow, including unipotent (CFU-GM, BFU-E) and pluripotent progenitors (CFU-GEMM, CFU-Mix and CFU-blast); as well as stromal cell precursors, terminal deoxynucleotidyl transferase (TdT) expressing B- and T-lymphoid precursors, early myeloid cells and early erythroid cells.

In a preferred embodiment, the cell, e.g., the 69039-expressing cell, is a bone marrow erythroid cell, e.g., an erythroid progenitor (e.g., a glycophorin A expressing cell) or a differentiated cell, e.g., an erythrocyte or a megakaryocyte.

In one embodiment, the hematopoietic cell is a lymphoid cell, e.g., B cells, and their precursors, T cells (e.g., $CD4^+8^+$ T cells, $CD4^+8^-$ T cells (e.g., helper T cells), $CD4^-CD8^+$ T cells (e.g., cytotoxic T cells), $CD4^-8^-$ T cells, and natural killer T cells) and their precursors.

In other embodiments, the cell is a neural cell, e.g., a neuron or glial cell (e.g., a cortical or hypothalamic neuron or glial cell. In yet another embodiment, the cell is a skin cell.

In a preferred embodiment, the cell, e.g., the 69039-expressing cell, is further contacted with a protein, e.g., a cytokine or a hormone. Exemplary proteins include, but are not limited to, G-CSF, GM-CSF, stem cell factor, interleukin-3 (IL-3), IL-4, Flt-3 ligand, thrombopoietin, and erythropoietin. Most preferably, the protein is erythropoietin. The protein contacting step can occur before, at the same time, or after the agent is contacted. The protein contacting step can be effected in vitro or ex vivo. For example, the cell, e.g., the 69039-expressing cell is obtained from a subject, e.g., a patient, and contacted with the protein ex vivo. The treated cell can be re-introduced into the subject. Alternatively, the protein contacting step can occur in vivo.

In one embodiment, the agent and the 69039-polypeptide or nucleic acid are contacted in vitro or ex vivo. Alternatively, the contacting step is effected in vivo in a subject, e.g., as part of a therapeutic or prophylactic protocol. Preferably, the subject is a human, e.g., a patient with an erythroid-associated disorder. For example, the subject can be a patient with an anemia, e.g., hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Alternatively, the subject can be a cancer patient, e.g., a patient with leukemic cancer, e.g., an erythroid leukemia, or a carcinoma, e.g., a renal carcinoma. In other embodiments, the subject is a non-human animal, e.g., an experimental animal. The contacting step(s) can be repeated.

In a preferred embodiment, the agent decreases the proliferation and/or enhances the differentiation of the cell, e.g., the 69039-expressing cell, e.g., the hematopoietic (e.g., the erythroid or myeloid) cell. Such agents can be used to treat or prevent cancers, e.g., leukemic cancers such as erythroid leukemias, or carcinomas, e.g., renal or lung carcinomas.

In a preferred embodiment, the agent increases the number of erythroid cells, by e.g., increasing the proliferation, survival, and/or stimulating the differentiation, of erythroid progenitor cells. Such agents can be used to treat or prevent anemias, e.g., hemolytic anemias, aberrant erythropoiesis, secondary anemias in non-hematolic disorders, anemias of chronic diseases such as chronic renal failure; endocrine deficiency diseases; and/or erythrocytosis (e.g., polycythemias).

In a preferred embodiment, the agent increases the number of erythroid cells, by e.g., increasing the proliferation, survival, and/or stimulating the differentiation, of granulocytic and monocytic progenitor cells, e.g., CFU-GM, CFU-G (colony forming unit—granulocyte), myeloblast, promyelocyte, myclocyte, a metamyelocyte, or a band cell. Such compounds can be used to treat or prevent neutropenia and granulocytopenia, e.g., conditions caused by cytotoxic chemotherapy, AIDS, congenital and cyclic neutropenia, myelodysplastic syndromes, or aplastic anemia.

In another aspect, the invention features a method of modulating hematopoiesis, e.g., erythropoiesis, comprising contacting a hematopoietic cell, e.g., a blood cell, such as an erythroid cell, with a agent that increases or decreases the activity or expression of a 69039 polypeptide or nucleic acid, thereby modulating the differentiation of the hematopoietic cell, e.g., the blood cell.

In a preferred embodiment, the 69039 polypeptide has an amino acid sequence identical to, or substantially identical to, SEQ ID NO:2. In other embodiments, the 69039 polypeptide is a fragment of at least 15, 20, 50, 100, 150, or more contiguous amino acids of SEQ ID NO:2.

In a preferred embodiment, the 69039 nucleic acid has a nucleotide sequence identical to, or substantially identical to, SEQ ID NO:1 or 3. In other embodiments, the 69039 nucleic acid is a fragment of at least 50, 100, 150, 200, 250, 300, 350, 400, 450, 500, or more contiguous nucleotides of SEQ ID NO:1 or 3.

In a preferred embodiment, the agent the agent modulates (e.g., increases or decreases) one or more of: proliferation/differentiation of a 69039-expressing cell; intracellular $Ca^{2+}$ concentration; or $Na^+$-dependent inactivation and $Ca^{2+}$-dependent regulation of a 69039 polypeptide; ion, e.g., sodium or calcium, flux across a cell membrane.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 69039 nucleic acid, or any combination thereof.

In a preferred embodiment, the agent is administered in combination with a second agent, e.g., a cytotoxic agent, a growth factor, or a cytokine.

In a preferred embodiment, the hematopoietic cell is an erythroid or a myeloid cell, e.g., an erythroid or myeloid progenitor or differentiated cell, e.g., an erythrocyte or a megakaryocyte.

In a preferred embodiment, the hematopoietic cell is a bone marrow CD34-expressing cell.

In a preferred embodiment, the agent and the 69039-polypeptide or nucleic acid are contacted in vitro or ex vivo.

In a preferred embodiment, the contacting step is effected in vivo in a subject, e.g., as part of a therapeutic or prophylactic protocol. Preferably, the subject is a human, e.g., a patient with a hematopoietic disorder such as an erythroid or myeloid-associated disorder. For example, the subject can be a patient with an anemia, e.g., a drug-induced anemia (e.g., a chemotherapy-induced anemia), hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Preferably, the erythroid-associated disorder is a drug-induced anemia (e.g., a chemotherapy induced anemia). Alternatively, the subject can be a cancer patient, e.g., a patient with leukemic cancer, e.g., an erythroid or myeloid leukemia. In other embodiments, the subject is a non-human animal, e.g., an experimental animal.

In a preferred embodiment, the method further includes contacting of the erythroid cell with a protein, e.g., a hormone. The protein can be a member of the following non-limiting group: G-CSF, GM-CSF, stem cell factor, interleukin-3 (IL-3), IL-4, Flt-3 ligand, thrombopoietin, and erythropoietin. More preferably, the protein is erythropoietin. The protein contacting step can occur before, at the same time, or after the agent is contacted. The protein contacting step can be effected in vitro or ex vivo. For example, the cell, e.g., the erythroid cell can be obtained from a subject, e.g., a patient, and contacted with the protein ex vivo. The treated cell can be re-introduced into the subject. Alternatively, the protein contacting step can occur in vivo. The contacting step(s) can be repeated.

In a preferred embodiment, the agent increases the number of hematopoietic cells, e.g., erythroid or myeloid cells, by e.g., increasing the proliferation, survival, and/or stimulating the differentiation, of hematopoietic (e.g., erythroid or myeloid) progenitor cells, in the subject. Such agents can be used to treat an anemia, e.g., a drug-(e.g., chemotherapy-) induced anemia, hemolytic anemia, aberrant erythropoiesis, secondary anemia in non-hematolic disorder, anemia of chronic diseases such as chronic renal failure; endocrine deficiency disease; and/or erythrocytosis (e.g., polycythemias).

In a preferred embodiment, the agent increases the number of erythroid or myeloid cells, by e.g., increasing the proliferation, survival, and/or stimulating the differentiation, of granulocytic and monocytic progenitor cells, e.g., CFU-GM, CFU-G (colony forming unit—granulocyte), myeloblast, promyelocyte, myelocyte, a metamyelocyte, or a band cell. Such compounds can be used to treat or prevent neutropenia and granulocytopenia, e.g., conditions caused by cytotoxic chemotherapy, AIDS, congenital and cyclic neutropenia, myelodysplastic syndromes, or aplastic anemia.

In yet another aspect, the invention features a method of treating or preventing a hematopoietic disorder, e.g., a myeloid- or an erythroid-associated disorder, in a subject. The method includes administering to the subject an effective amount of an agent that modulates the activity or expression of a 69039 polypeptide or nucleic acid such that the hematopoietic disorder is ameliorated or prevented.

In a preferred embodiment, the 69039 polypeptide has an amino acid sequence identical to, or substantially identical to, SEQ ID NO:2. In other embodiments, the 69039 polypeptide is a fragment of at least 15, 20, 50, 100, 150, or more contiguous amino acids of SEQ ID NO:2.

In a preferred embodiment, the 69039 nucleic acid has a nucleotide sequence identical to, or substantially identical to, SEQ ID NO:1 or 3. In other embodiments, the 69039 nucleic acid is a fragment of at least 50, 100, 150, 200, 250, 300, 350, 400, 450, 500, or more contiguous nucleotides of SEQ ID NO:1 or 3.

In a preferred embodiment, the agent the agent modulates (e.g., increases or decreases) one or more of: proliferation/differentiation of a 69039-expressing cell; intracellular $Ca^{2+}$ concentration; or $Na^+$-dependent inactivation and $Ca^{2+}$-dependent regulation of a 69039 polypeptide; ion, e.g., sodium or calcium, flux across a cell membrane.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 69039 nucleic acid, or any combination thereof.

In a preferred embodiment, the agent is administered in combination with a second agent, e.g., a cytotoxic agent, a growth factor, or a cytokine.

In a preferred embodiment, the subject is a human, e.g., a patient with a hematopoietic disorder, e.g., a myeloid- or an erythroid-associated disorder. For example, the subject can be a patient with an anemia, e.g., a drug-(chemotherapy-) induced anemia, hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Preferably, the anemia is a drug-(chemotherapy-) induced anemia. Alternatively, the subject can be a cancer patient, e.g., a patient with leukemic cancer, e.g., an erythroid leukemia, or a patient with a carcinoma, e.g., a renal carcinoma. In other embodiments, the subject is a non-human animal, e.g., an experimental animal.

In a preferred embodiment, the agent decreases the proliferation and/or enhances the differentiation of a cell, e.g., a 69039-expressing cell, e.g., a hematopoietic cell (e.g., a myeloid or an erythroid cell), in the subject. Such agents can be used to treat or prevent cancers, e.g., leukemic cancers such as erythroid leukemias, or carcinomas, e.g., renal carcinomas.

In a preferred embodiment, the agent increases the number of hematopoietic cells, e.g., blood cells (e.g., erythroid cells), by e.g., increasing the proliferation, and/or stimulating the differentiation, of erythroid progenitor cells, in the subject. Such agents can be used to treat an anemia, e.g., a drug-(chemotherapy-) induced anemia, a hemolytic anemia, aberrant erythropoiesis, a secondary anemia in non-hematolic disorder, anemia of chronic diseases such as chronic renal failure; endocrine deficiency disease; and/or erythrocytosis (e.g., polycythemias).

In a preferred embodiment, the agent increases the number of myeloid or erythroid cells, by e.g., increasing the proliferation, survival, and/or stimulating the differentiation, of granulocytic and monocytic progenitor cells, e.g., CFU-GM, CFU-G (colony forming unit—granulocyte), myeloblast, promyelocyte, myelocyte, a metamyelocyte, or a band cell. Such compounds can be used to treat or prevent neutropenia and granulocytopenia, e.g., conditions caused by cytotoxic chemotherapy, AIDS, congenital and cyclic neutropenia, myelodysplastic syndromes, or aplastic anermia.

In a preferred embodiment, the disorder is a hematopoietic disorder, e.g. a myeloid or an erythroid-associated disorder. Examples of erythroid-associated disorder include drug-(chemotherapy-) induced anemia, hemolytic anemia, aberrant erythropoiesis, secondary anemia in non-hematolic disorders, anemia of chronic disease such as chronic renal failure; endocrine deficiency disease; and/or erythrocytosis (e.g., polycythemia). Preferably, the erythroid-associated disorder is a drug-(chemotherapy-) induced anemia.

In a preferred embodiment, the disorder is a cancer, e.g., a leukemic cancer, e.g., an erythroid leukemia, or a carcinoma, e.g., a renal carcinoma.

In a preferred embodiment, the method further includes administering an effective amount of a protein, e.g., a cytokine or a hormone, to the subject. Exemplary proteins include, but are not limited to, G-CSF, GM-CSF, stem cell factor, interleukin-3 (IL-3), IL-4, Flt-3 ligand, thrombopoietin, and erythropoietin. Preferably, the protein is erythropoietin. The protein can be administered before, at the same time or after, administration of the agent.

The administration of the agent and/or protein can be repeated.

In still another aspect, the invention features a method for evaluating the efficacy of a treatment of a disorder, in a subject. The method includes treating a subject with a protocol under evaluation; assessing the expression of a 69039 nucleic acid or 69039 polypeptide, such that a change in the level of 69039 nucleic acid or 69039 polypeptide after treatment, relative to the level before treatment, is indicative of the efficacy of the treatment of the disorder.

In a preferred embodiment, the disorder is a hematopoietic disorder, e.g., a myeloid or an erythroid-associated disorder. Examples of erythroid-associated disorders include an anemia, e.g., a drug-(e.g., chemotherapy-) induced anemia, a hemolytic anemia, aberrant erythropoiesis, secondary anemia in non-hematolic disorder, anemias of chronic disease such as chronic renal failure; endocrine deficiency diseases; and/or erythrocytosis (e.g., polycythemia).

In a preferred embodiment, the disorder is a cancer, e.g., leukemic cancer, e.g., an erythroid leukemia, or a carcinoma, e.g., a renal carcinoma.

In a preferred embodiment, the subject is a human.

In a preferred embodiment, the subject is an experimental animal, e.g., an animal model for a hematopoietic-(e.g., an erythroid-) associated disorder.

In a preferred embodiment, the method can further include treating the subject with a protein, e.g., a cytokine or a hormone. Exemplary proteins include, but are not limited to, G-CSF, GM-CSF, stem cell factor, interleukin-3 (IL-3), IL-4, Flt-3 ligand, thrombopoietin, and erythropoietin. Preferably, the protein is erythropoietin.

The invention also features a method of diagnosing a disorder, e.g., hematopoietic disorder (e.g., an erythroid-associated disorder), in a subject. The method includes evaluating the expression or activity of a 69039 nucleic acid or a 69039 polypeptide, such that, a difference in the level of 69039 nucleic acid or 69039 polypeptide relative to a normal subject or a cohort of normal subjects is indicative of the disorder.

In a preferred embodiment, the subject is a human.

In a preferred embodiment, the evaluating step occurs in vitro or ex vivo. For example, a sample, e.g., a blood sample, is obtained from the subject.

In a preferred embodiment, the evaluating step occurs in vivo. For example, by administering to the subject a detectably labeled agent that interacts with the 69039 nucleic acid or polypeptide, such that a signal is generated relative to the level of activity or expression of the 69039 nucleic acid or polypeptide.

In a preferred embodiment, the disorder is a hematopoietic disorder, e.g., a hematopoietic disorder as described herein. In other embodiments, the disorder is an erythroid-associated disorder, e.g., an erythroid-associated disorder as described herein.

The invention also provides assays for determining the activity of or the presence or absence of 69039 polypeptides or nucleic acid molecules in a biological sample, including for disease diagnosis.

In further aspect, the invention provides assays for determining the presence or absence of a genetic alteration in a 69039 polypeptide or nucleic acid molecule, including for disease diagnosis.

In yet another aspect, the invention features a method for identifying an agent, e.g., a compound, which modulates the activity of a 69039 polypeptide, e.g., a 69039 polypeptide as described herein, or the expression of a 69039 nucleic acid, e.g., a 69039 nucleic acid as described herein, including contacting the 69039 polypeptide or nucleic acid with a test agent (e.g., a test compound); and determining the effect of the test compound on the activity of the polypeptide or nucleic acid to thereby identify a compound which modulates the activity of the polypeptide or nucleic acid.

In a preferred embodiment, the activity is one or more of: proliferation/differentiation of a 69039-expressing cell; intracellular $Ca^{2+}$ concentration; or $Na^+$-dependent inactivation and $Ca^{2+}$-dependent regulation of a 69039 polypeptide; ion, e.g., sodium or calcium, flux across a cell membrane.

In a preferred embodiment, the activity of the 69039 polypeptide is hematopoiesis, e.g., erythropoiesis.

In a preferred embodiment, the activity of the 69039 polypeptide is proliferation, differentiation, and/or survival of a cell, e.g., a 69039-expressing cell, e.g., a hematopoietic cell (e.g., a bone marrow cell such as a CD34 positive cell, an erythroid cell, a megakaryocyte).

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or a 69039 nucleic acid, or any combination thereof.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 69039 molecule. In one embodiment, the capture probe is a nucleic acid, e.g., a probe complementary to a 69039 nucleic acid sequence. In another embodiment, the capture probe is a polypeptide, e.g., an antibody specific for 69039 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIG. 2 depicts an alignment of the $Na^+/Ca^{2+}$ exchanger domain of human 69039 with a consensus amino acid sequence derived from a hidden Markov model (HMM) from PFAM. The upper sequence is the consensus amino acid sequence (SEQ ID NO:4), while the lower amino acid sequence corresponds to amino acids 110 to 257 of SEQ ID NO:2.

FIG. 3 depicts an alignment of the Calx-θ motif of human 69039 with a consensus amino acid sequence derived from a hidden Markov model (HMM) from SMART. The upper sequence is the consensus amino acid sequence (SEQ ID NO:5), while the lower amino acid sequence corresponds to amino acids 385 to 485, and 519 to 594 of SEQ ID NO:2.

In FIG. 5A, 69039 mRNA was highly expressed in CD34-expressing populations (CD34+) of cells from human hematological tissues, such as cord blood CD34+, mPB CD34+, mBM CD34+, or BM CD34+; as well as in brain cells. 69039 mRNA expression was barely observed in bone marrow glycophorin A (GPA)-expressing cells. In FIG. 5B, mRNA expression was detected at the indicated times in culture (e.g., 24 hr, 48 hr, or 6 days, 12 days in culture). High levels of 69039 mRNA expression were observed in one sample of Mast cells, in erythroid cells, especially day 0, and hr 24, or in erythropoietin treated erythroid burst forming units (BFUs), especially day 7. In FIG. 5C, mRNA expression was detected at the indicated times in culture. High levels of 69039 mRNA expression were observed in megakaryocytes, especially day 0, hr 24, and day 12, or in neutrophils cells, escpeically day 0. The relative tissue distribution of 69039 mRNA is depicted in tabular form in Tables 3–5.

DETAILED DESCRIPTION

Figure 1:
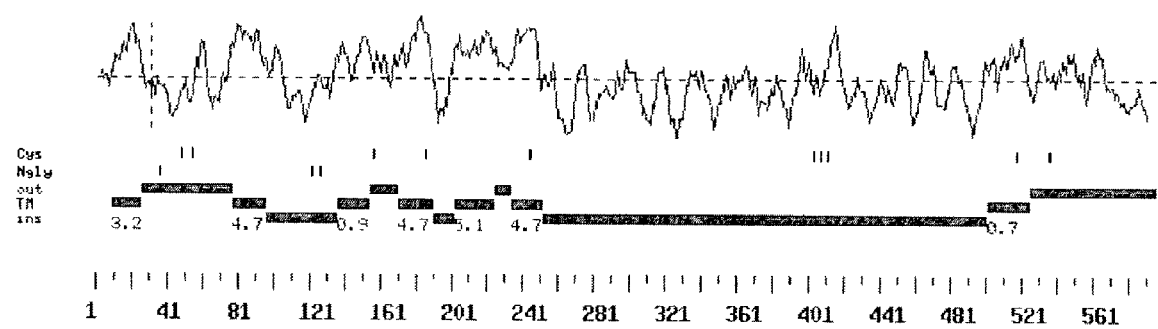
FIG. 1 depicts a hydropathy plot of human 69039. Relative hydrophobic residues are shown above the dashed horizontal line, and relative hydrophilic residues are below the dashed horizontal line. Numbers corresponding to positions in the amino acid sequence of human 69039 are indicated. Polypeptides of the invention include fragments which include: all or part of a hydrophobic sequence, i.e., a sequence above the dashed line, e.g., the sequence from about amino acid 58 to 68, from about 410 to 420, and from about 557 to 565 of SEQ ID NO:2; all or part of a hydrophilic sequence, i.e., a sequence below the dashed line, e.g., the sequence of from about amino acid 260 to 275, from about 320 to 335, and from about 487 to 500 of SEQ ID NO:2.

The human 69039 sequence (see SEQ ID NO:1, as recited in Example 1), which is approximately 2534 nucleotides long including untranslated regions, contains a predicted methionine-initiated coding sequence of about 1788 nucleotides, including the termination codon. The coding sequence encodes a 595 amino acid protein (see SEQ ID NO:2, as recited in Example 1). The human 69039 protein of SEQ ID NO:2 includes an amino-terminal hydrophobic amino acid sequence, consistent with a signal sequence, of about 31 amino acids (from amino acid 1 to about amino acid 31 of SEQ ID NO:2), which upon cleavage results in the production of a mature protein form. This mature protein form is approximately 564 amino acid residues in length (from about amino acid 32 to amino acid 595 of SEQ ID NO:2).

Human 69039 contains the following regions or other structural features:

a predicted $Na^+/Ca^{2+}$ exchanger domain (PFAM Accession Number PF01699) located at about amino acids 110 to 257 of SEQ ID NO:2;

two predicted Calx-θ motifs located at about amino acids 385 to 485, and 519 to 594 of SEQ ID NO:2;

five predicted transmembrane segments located at about amino acids 77 to 95, 136 to 153, 170 to 189, 202 to 224, and 234 to 251 of SEQ ID NO:2;

one predicted N-terminal extracellular domain located at about amino acids 31 to 76 of SEQ ID NO:2;

one predicted C-terminal cytoplasmic domain located at about amino acids 252 to 595 of SEQ ID NO:2;

two predicted cytoplasmic loops located at about amino acids 96 to 135, and 190 to 201 of SEQ ID NO:2;

two predicted extracellular loops located at about amino acids 154 to 169, and 225 to 233 of SEQ ID NO:2;

three predicted N-glycosylation sites (PS00001) located at about amino acids 45 to 48, 130 to 133, and 135 to 138 of SEQ ID NO:2;

one predicted cAMP- and cGMP-dependent protein kinase phosphorylation site (PS00004) located at about amino acids 378 to 381 of SEQ ID NO:2;

seven predicted Protein Kinase C phosphorylation sites (PS00005) at about amino acids 113 to 115, 125 to 127, 194 to 196, 267 to 269, 312 to 314, 460 to 462, and 572 to 574 of SEQ ID NO:2;

ten predicted Casein Kinase II phosphorylation sites (PS00006) located at about amino acids 69 to 72, 106 to 109, 144 to 147, 277 to 280, 312 to 315, 382 to 385, 460 to 463, 522 to 525, 583 to 586 of SEQ ID NO:2;

one predicted Tyrosine kinase phosphorylation site (PS00007) from about amino acids 397 to 405 of SEQ ID NO:2: and six predicted N-myristylation sites (PS00008) from about amino acids 50 to 55, 422 to 427, 438 to 443, 497 to 502, 557 to 562, and 571 to 576 of SEQ ID NO:2.

For general information regarding PFAM identifiers, PS prefix and PF prefix domain identification numbers, refer to Sonnhammer et al. (1997) *Protein* 28: 405–420 and http://www.psc.edu/general/ software/packages/pfam/pfam.html.

TABLE 1

Summary of transmembrane domains.

| Transmembrane segment located in SEQ ID NO: 2 | Cytoplasmic sequence located in SEQ ID NO: 2 | Extracellular sequence located in SEQ ID NO: 2 |
|---|---|---|
| about 77 to 95 | | about 31 to 76 (N-terminal) |
| about 136 to 153 | about 96 to 135 | |
| about 170 to 189 | | about 154 to 169 |
| about 202 to 224 | about 190 to 201 | |
| about 234 to 251 | | about 225 to 233 |
| | about 252 to 594 (C-terminal) | |

The 69039 protein contains a significant number of structural characteristics in common with members of the $Na^+/Ca^{2+}$ exchanger family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A $Na^+/Ca^{2+}$ exchanger family of proteins is characterized by about 11 I-helical transmemebrane segments (TMS). An amino-terminal hydrophobic domain (TMS1–5) is separated from a carboxyl-terminal domain (TMS6–11) by a long cytomplasmic loop. The amino terminus has been shown to be extracellular. The 69039 polypeptide includes the first five transmembrane segments and the long cytoplasmic loop. The importance of cysteine residues in the $Na^+/Ca^{2+}$ exchanger has been examined previously. Disulfide bonds are present in the exchanger as determined by gel mobility differences under reducing and nonreducing conditions in mutant and wild-type exchanger preparations. Redox modification of the exchanger stimulated activity and suggested that the stimulation was due to a rearrangement of disulfide bonds. See, e.g., Nicoll et al. (1999) *J. Biol. Chem.* 274: 910–917. The $Na^+/Ca^{2+}$ exchangers are found in diverse metazoan tissues, including heart, brain, and skeletal muscles. They have a low affinity but a high capacity for intracellular calcium, and modulate free $Ca^{2+}$ concentration.

A 69039 polypeptide can include a "$Na^+/Ca^{2+}$ exchanger domain" or regions homologous with a "$Na^+/Ca^{2+}$ exchanger domain."

As used herein, the term "Na/Ca exchanger domain" includes an amino acid sequence of about 50 to 300 amino acid residues in length and having a bit score for the alignment of the sequence to the Na/Ca exchanger domain profile (Pfam HMM) of at least 50. Preferably, it modulates free $Ca^{2+}$ concentration in cells. Preferably, a $Na^+/Ca^{2+}$ exchanger domain includes at least about 70 to 250 amino acids, more preferably about 100 to 200 amino acid residues, or about 140 to 160 amino acids and has a bit score for the alignment of the sequence to the $Na^+/Ca^{2+}$ exchanger domain (HMM) of at least XX or greater. The $Na^+/Ca^{2+}$ exchanger domain (HMM) has been assigned the PFAM Accession Number PF01699 (http://genome.wustl.edu/Pfam/.html). An alignment of the $Na^+/Ca^{2+}$ exchanger domain (amino acids 110 to 257of SEQ ID NO:2) of human 69039 with a consensus amino acid sequence (SEQ ID NO:4) derived from a hidden Markov model is depicted in FIG. 2.

In a preferred embodiment 69039 polypeptide or protein has a "Na⁺/Ca²⁺ exchanger domain" or a region which includes at least about 70 to 250 more preferably about 100 to 200, or 140 to 160 amino acid residues and has at least about 50%, 60%, 70% 80% 90% 95%, 99%, or 100% homology with a "Na⁺/Ca²⁺ exchanger domain,"e.g., the Na⁺/Ca²⁺ exchanger domain of human 69039 (e.g., residues 110 to 257 of SEQ ID NO:2).

To identify the presence of a "Na⁺/Ca²⁺ exchanger" domain in a 69039 protein sequence, and make the determination that a polypeptide or protein of interest has a particular profile, the amino acid sequence of the protein can be searched against the Pfam database of HMMs (e.g., the Pfam database, release 2.1) using the default parameters (http://www.sanger.ac.uk/Software/PfamHMM_search).
For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405–420 and a detailed description of s can be found, for example, in Gribskov et al.(1990) *Meth. Enzymol.* 183: 146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference. A search was performed against the HMM database resulting in the identification of a "Na⁺/Ca²⁺ exchanger domain" in the amino acid sequence of human 69039 at about residues 110 to 257 of SEQ ID NO:2 (see FIG. 2).

A 69039 molecule can further include at least one or two Calx-θ motifs. An isolated Calx-θ motif exists in exchanger proteins, as well as in mammalian integrin-θ4 and in three Synechocystis proteins of unknown function. In both exchangers and mammalian integrin-θ4, Calx-θ motifs are predicted to be cytoplasmic. It has been shown that Calx-θ motifs in NCX1 contain a high-affinity Ca²⁺ binding site. They also overlap a region required for inhibition of NCX1 by elevated intracellular sodium, the same region may also bind ankyrin. See, e.g., Schwarz & Benzer (1997) *J. Biol. Chem.* 94: 10249–10254. Calx-θ motifs have a series of θ-strands and turns.

As used herein, a "Calx-θ motif" includes an amino acid sequence of about 20 to 300 amino acid residues in length that is involved in Ca²⁺ binding and intracellular signal transducing. Preferably, the Calx-θ motif is located at the C-terminal cytoplasrmic region of the 69039 polypeptide. The term "Calx-θ motif" includes an amino acid sequence of about 20 to 300 amino acid residues in length and having a bit score for the alignment of the sequence to the cyclic nucleotide binding domain (HMM) of at least 50. Preferably, a Calx-θ motif includes at least about 50 to 200 amino acids, more preferably about 70 to 150 amino acid residues, or about 90 to 110 amino acids and has a bit score for the alignment of the sequence to the Calx-θ motif (HMM) of at least 100, 130, or 150 or greater. The Calx-θ motif (HMM) has been assigned the Calx_beta in SMART. An alignment of the Calx-θ motif (amino acids 385 to 485 of SEQ ID NO:2) of human 69039 with a consensus amino acid sequence (SEQ ID NO:5) derived from a hidden Markov model is depicted in FIG. 3.

In a preferred embodiment, a 69039 polypeptide or protein has a "Calx-θ motif" or a region which includes at least about 20 to 300, more preferably about 50 to 200, 70 to 150, or 90 to 110 amino acid residues and has at least about 50%, 60%, 70% 80% 90% 95%, 99%, or 100% homology with a "Calx-θ motif," e.g., the Calx-θ motif of human 69039 (e.g., residues 385 to 485 of SEQ ID NO:2).

The "Calx-θ motif" also includes an amino acid sequence of about 20 to 300 amino acid residues in length and having a bit score for the alignment of the sequence to the cyclic nucleotide binding domain (HMM) of at least 30. Preferably, a Calx-θ motif includes at least about 40 to 150 amino acids, more preferably about 50 to 100 amino acid residues, or about 70 to 80 amino acids and has a bit score for the alignment of the sequence to the Calx-θ motif (HMM) of at least 50, 60, or 70 or greater. The Calx-θ motif (HMM) has been assigned the Calx_beta in SMART. An alignment of the Calx-θ motif (amino acids 519 to 594 of SEQ ID NO:2) of human 69039 with a consensus amino acid sequence (SEQ ID NO:5) derived from a hidden Markov model is depicted in FIG. 3.

In a preferred embodiment, a 69039 polypeptide or protein has a "Calx-θ motif" or a region which includes at least about 40 to 150, more preferably about 50 to 100, or 70 to 80 amino acid residues and has at least about 50%, 60%, 70% 80% 90% 95%, 99%, or 100% homology with a "Calx-θ motif," e.g., the Calx-θ motif 69039 (e.g., residues 519 to 594 of SEQ ID NO:2).

To identify the presence of a "Calx-θ motif" domain in a 69039 protein sequence, and make the determination that a polypeptide or protein of interest has a particular profile, the amino acid sequence of the protein can be searched against a SMART database (Simple Modular Architecture Research Tool, http://smart.embl-heidelberg.de/) of HMMs as described in Schultz et al. (1998), *Proc. Natl. Acad. Sci. USA* 95:5857 and Schultz et al. (200) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids*. Cambridge University Press.; http://hmmer.wustl.edu/). The database also is extensively annotated and monitored by experts to enhance accuracy. A search was performed against the HMM database resulting in the identification of a "Calx-θ motif" domain in the amino acid sequence of human 69039 at about residues 385 to 485 and 519 to 594 of SEQ ID NO:2 (see FIG. 3).

A 69039 protein can further include a signal peptide, and is predicted to be a secreted protein. As used herein, a "signal peptide" or "signal sequence" refers to a peptide of about 10 to 40, preferably about 15 to 25, more preferably, about 21 amino acid residues in length which occurs at the N-terminus of secretory and integral membrane proteins and which contains a majority of hydrophobic amino acid residues. For example, a signal sequence contains at least about 10 to 50, preferably about 25 to 35, more preferably, 31 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide," serves to direct a protein containing such a sequence to a lipid bilayer. For example, in one embodiment, a 14063 protein contains a signal sequence of about amino acids 1 to 30 of SEQ ID NO:2. The "signal sequence"

is cleaved during processing of the mature protein. The mature 69039 protein corresponds to amino acids 31 to 595 of SEQ ID NO:2.

A 69039 protein further includes a predicted N-terminal extracellular domain located at about amino acids 31 to 76 of SEQ ID NO:2. As used herein, a "N-terminal extracellular domain" includes an amino acid sequence having about 1 to 200, preferably about 1 to 100, or even more preferably about 1 to 50 amino acid residues in length and is located outside of a cell or extracellular. The C-terminal amino acid residue of a "N-terminal extracellular domain" is adjacent to a N-terminal amino acid residue of a transmembrane domain in a 69039 protein. For example, a N-terminal extracellular domain is located at about amino acid residues 31 to 76 of SEQ ID NO:2.

In a preferred embodiment 69039 polypeptide or protein has an "N-terminal extracellular domain" or a region which includes at least about 1 to 200, preferably about 1 to 50, and even more preferably about 46 amino acid residues and has at least about 60%, 70% 80% 90% 95%, 99%, or 100% homology with an "N-terminal extracellular domain," e.g., the N-terminal extracellular domain of human 69039 (e.g., residues 31 to 76 of SEQ ID NO:2).

In another embodiment, a 69039 protein includes a "C-terminal cytoplasmic domain," also referred to herein as a C-terminal cytoplasmic tail, in the sequence of the protein. As used herein, a "C-terminal cytoplasmic domain" includes an amino acid sequence having a length of at least about 200, more preferably 300 or more amino acid residues and is located within a cell or within the cytoplasm of a cell. Accordingly, the N-terminal amino acid residue of a "C-terminal cytoplasmic domain" is adjacent to a C-terminal amino acid residue of a transmembrane domain in a naturally-occurring 69039 protein. For example, a C-terminal cytoplasmic domain is found at about amino acid residues 252 to 595 of SEQ ID NO:2.

In a preferred embodiment, a 69039 polypeptide or protein has a C-terminal cytoplasmic domain or a region which includes at least about 200, more preferably 300 or more amino acid residues and has at least about 60%, 70% 80% 90% 95%, 99%, or 100% homology with an "C-terminal cytoplasmic domain," e.g., the C-terminal cytoplasmic domain of human 69039 (e.g., residues 252 to 595 of SEQ ID NO:2).

69039 proteins can further include at least one, two, three, four, and preferably five transmembrane domains. As used herein, the term "transmembrane domain" includes an amino acid sequence of about 10 to 45, preferably 12 to 30, and most preferably 15 to 25, amino acid residues in length that spans the plasma membrane. More preferably, a transmembrane domain includes about at least 18, 19, 20, or 23 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Annual Rev. Neurosci.* 19: 235–263, the contents of which are incorporated herein by reference. Amino acid residues 77 to 95, 136 to 153, 170 to 189, 202 to 224, and 234 to 251 of SEQ ID NO:2 are transmembrane domains (see FIG. 1). Accordingly, proteins having at least 50–60% homology, preferably about 60–70%, more preferably about 70–80%, about 80–90%, or about 90–100% homology with amino acids 77 to 95, 136 to 153, 170 to 189, 202 to 224, and 234 to 251 of SEQ ID NO:2 are within the scope of the invention.

In another embodiment, a 69039 protein includes at least one, or two cytoplasmic loops, also referred to herein as a cytoplasmic domain. As used herein, a "cytoplasmic loop" includes an amino acid sequence having a length of at least about 10 amino acid residues located within a cell or within the cytoplasm of a cell. For example, a cytoplasmic loop is found at about amino acids 96 to 135, or 190 to 201 of SEQ ID NO:2.

In a preferred embodiment 69039 polypeptide or protein has at least one or two cytoplasmic loops or regions which includes at least about 10 amino acid residues and has at least about 60%, 70% 80% 90% 95%, 99%, or 100% homology with an "cytoplasmic loop," e.g., at least one cytoplasmic loop of human 69039 (e.g., residues 96 to 135, or 190 to 201 of SEQ ID NO:2).

In another embodiment, a 69039 protein include at least one, or two extracellular loop. As defined herein, the term "loop" includes an amino acid sequence that resides outside of a phospholipid membrane, having a length of at least about 20 to 70, and preferably about 30 to 50 amino acid residues, and has an amino acid sequence that connects two transmembrane domains within a protein or polypeptide. Extracellular domains are located outside of the cell. Accordingly, the N-terminal amino acid of a non-cytoplasmic loop is adjacent to a C-terminal amino acid of a transmembrane domain in a 69039 protein, and the C-terminal amino acid of a non-cytoplasmic loop is adjacent to an N-terminal amino acid of a transmembrane domain in a 69039 protein. For example, an "extracellular loop" can be found at about amino acids 154 to 169, and 225 to 233 of SEQ ID NO:2.

In a preferred embodiment, a 69039 polypeptide or protein has at least one, or two, extracellular loops or regions which include at least about 5, preferably about 5 to 80, and more preferably about 20 to 50 amino acid residues and has at least about 60%, 70% 80% 90% 95%, 99%, or 100% homology with an "non-cytoplasmic loop," e.g., at least one non-cytoplasmic loop of human 33751 (e.g., residues 154 to 169, and 225 to 233 of SEQ ID NO:2).

Accordingly, in one embodiment of the invention, a 69039 includes at least one signal peptide, at least one, two, three, four, preferably five, transmembrane domains, at least one, or two cytoplasmic loops, and/or at least one, or two extracellular loops. In another embodiment, the 69039 polypeptide further includes an N-terminal extracellular domain and a C-terminal cytoplasmic domain.

A 69039 family member can include at least one predicted $Na^+/Ca^{2+}$ exchanger domain; and at least one, preferably two predicted Calx-θ motifs. Furthermore, a 69039 family member can include at least one predicted N-glycosylation sites (PS00001); at least one, two, three, or preferably four predicted cAMP- and cGMP-dependent protein kinase phosphorylation sites (PS00004); at least one, two, three, four, five, six, or seven, predicted protein kinase C phosphorylation sites (PS00005); at least one, two, three, four, five, six, seven, eight, nine, or ten predicted casein kinase II phosphorylation sites (PS00006); at least one predicted tyrosine kinase phosphorylation sites (PS00007); and at least one, two, three, four, five, or six predicted N-myristylation sites (PS00008).

As the 69039 polypeptides of the invention may modulate 69039-mediated activities, they may be useful as of for developing novel diagnostic and therapeutic agents for 69039-mediated or related disorders, as described below.

Based on the above-described sequence similarities and the tissue distribution described below, the 69039 molecules of the present invention are predicted to have similar biological activities as $Na^+/Ca^{2+}$ exchanger family members. $Na^+/Ca^{2+}$ exchanger proteins actively coordinate with $Ca^{2+}$ channels and $Ca^{2+}$ binding proteins to control the availability of these ions for $Ca^{2+}$-dependent cellular responses. For example, in an excitable or contractile cell, a stimulus activates $Ca^{2+}$ channels to allow rapid cytosolic influx of $Ca^{2+}$ and induce a response to the stimulus. After the stimulus is removed, a $Na^+/Ca^{2+}$ exchanger transports the $Ca^{2+}$ back out of the cytoplasm to restore the potential function of the cell. Alterations in the dynamic interplay of $Ca^{2+}$ influx and efflux processes play roles in many diseases. These diseases can be associated with an intracellular $Ca^{2+}$ overload, such as in MELAS, an encephalomyopathy (Moudy et al. (1995) *Proc. Natl. Acad. Sci. USA* 92:729–33), in retinal degeneration (Edward et al. (1991) *Arch. Opthalmol.* 109:554–62), or in myocardial reoxygenation/reperfusion injury (Mochizuki and Jiang (1998) *Jpn. Heart J.* 39:707–14); an intracellular potassium overload in a variant of Bartter's syndrome (Peleg et al. (1997) *Hypertension* 30:1338–41); or an intracellular $Ca^{2+}$ deficiency in stimulated platelets of some diabetic patients (Yamaguchi et al. (1991) *Diabetes Res.* 18:89–94).

As used herein, a "69039 activity", "biological activity of 69039" or "functional activity of 69039," refers to an activity exerted by a 69039 protein, polypeptide or nucleic acid molecule. For example, a 69039 activity can be an activity exerted by 69039 in a physiological milieu on, e.g., a 69039-responsive cell or on a 69039 substrate, e.g., a protein substrate. A 69039 activity can be determined in vivo or in vitro. In one embodiment, a 69039 activity is a direct activity, such as an association with a 69039 target molecule. A "target molecule" or "binding partner" is a molecule with which a 69039 protein binds or interacts in nature. A 69039 activity can also be an indirect activity, e.g., regulating proliferation/differentiation, modulating $Ca^{2+}$ concentration, or intracellular $Na^+$-dependent inactivation and $Ca^{2+}$-dependent regulation. In an exemplary embodiment, 69039 is controlling $Ca^{2+}$ influx and efflux processes.

Thus, in accordance with the invention, a 69039 $Na^+/Ca^{2+}$ exchanger or subsequence or variant polypeptide may have one or more domains and, therefore, one or more activities or functions characteristic of a $Na^+/Ca^{2+}$ exchanger family member, including, but not limited to: (1) transporting $Ca^{2+}$ across a membrane; (2) transport $Na^+$ across a membrane; (3) modulate intracellular $Na^+$-dependent inactivation and $Ca^{2+}$-dependent regulation; (4) modulate (e.g., stimulate) cell differentiation, e.g., differentiation of hematopoietic cells (e.g., differentiation of blood cells (e.g., erythroid progenitor cells, such as CD34+ erythroid progenitors)); (5) modulate hematopoiesis, e.g., erythropoiesis; (6) modulate cell proliferation, e.g., proliferation of hematopoietic cells (e.g., erythroid progenitor cells); (7) inactivate cell surface growth factor receptors, e.g., cytokine receptors; (8) modulate apoptosis, of a cell, e.g., increase apoptosis of a cancer cell, e.g., a leukemic cell, (e.g., an erythroleukemia cell); or suppress apoptosis of a blood or erythroid cell; or (9) modulate transcriptional activity, e.g., cytokine transcriptional activity.

Figure 4:
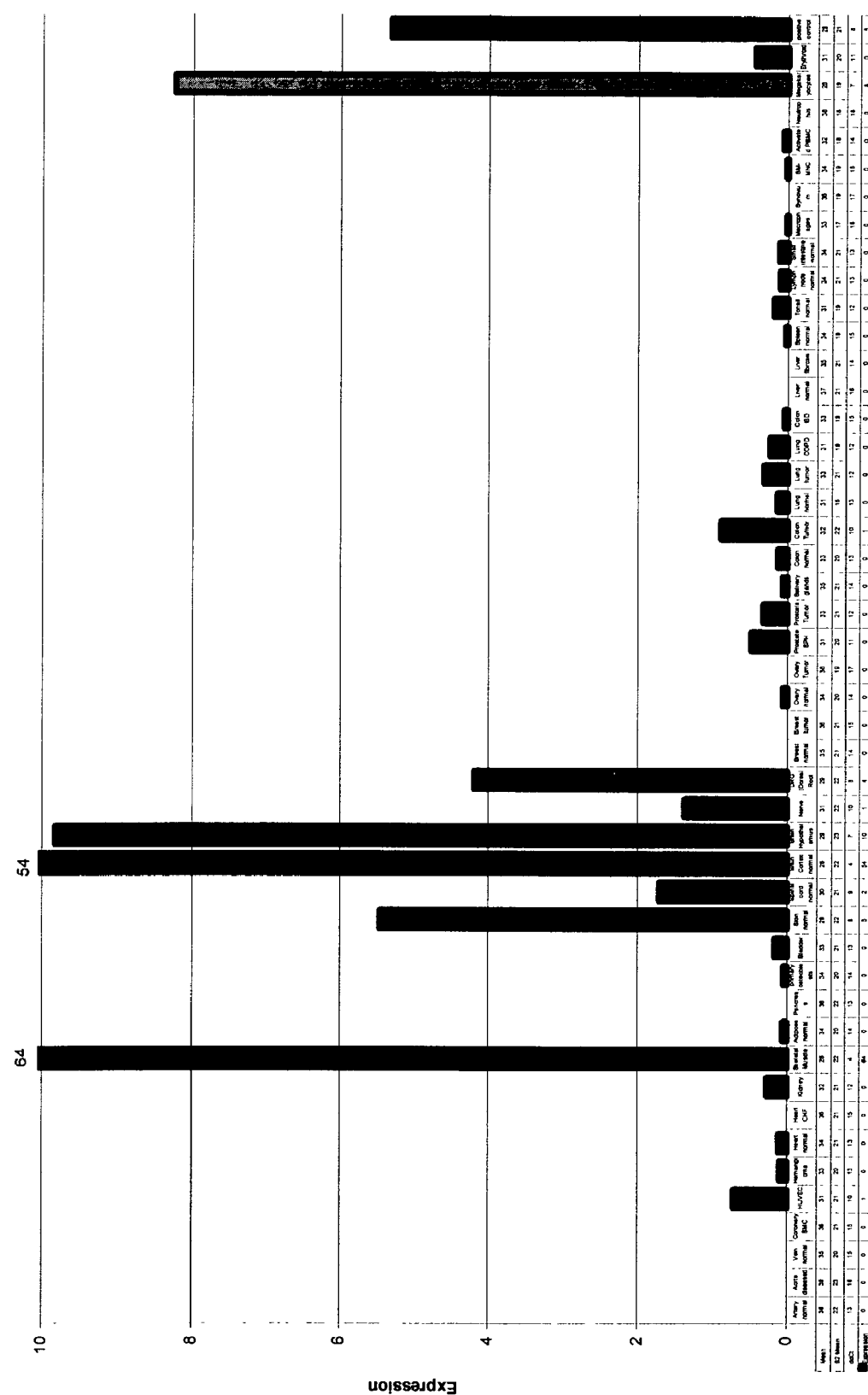
FIG. 4 is a bar graph depicting relative 69039 mRNA expression as determined by TaqMan assays in a panel of human tissues, including artery, heart, pancreas, skin, spinal cord, brain, dorsal root ganglia (DRG), nerve, breast, colon, lung, liver, megakaryocytes, and erythroid. The highest 69039 mRNA expression was observed in brain, skeletal muscle, followed by megakaryocytes, skin, dorsal root ganglia (DRG), spinal cord, and nerve. The relative tissue distribution of 69039 mRNA is depicted in tabular form in Table 2.
Figure 5A:
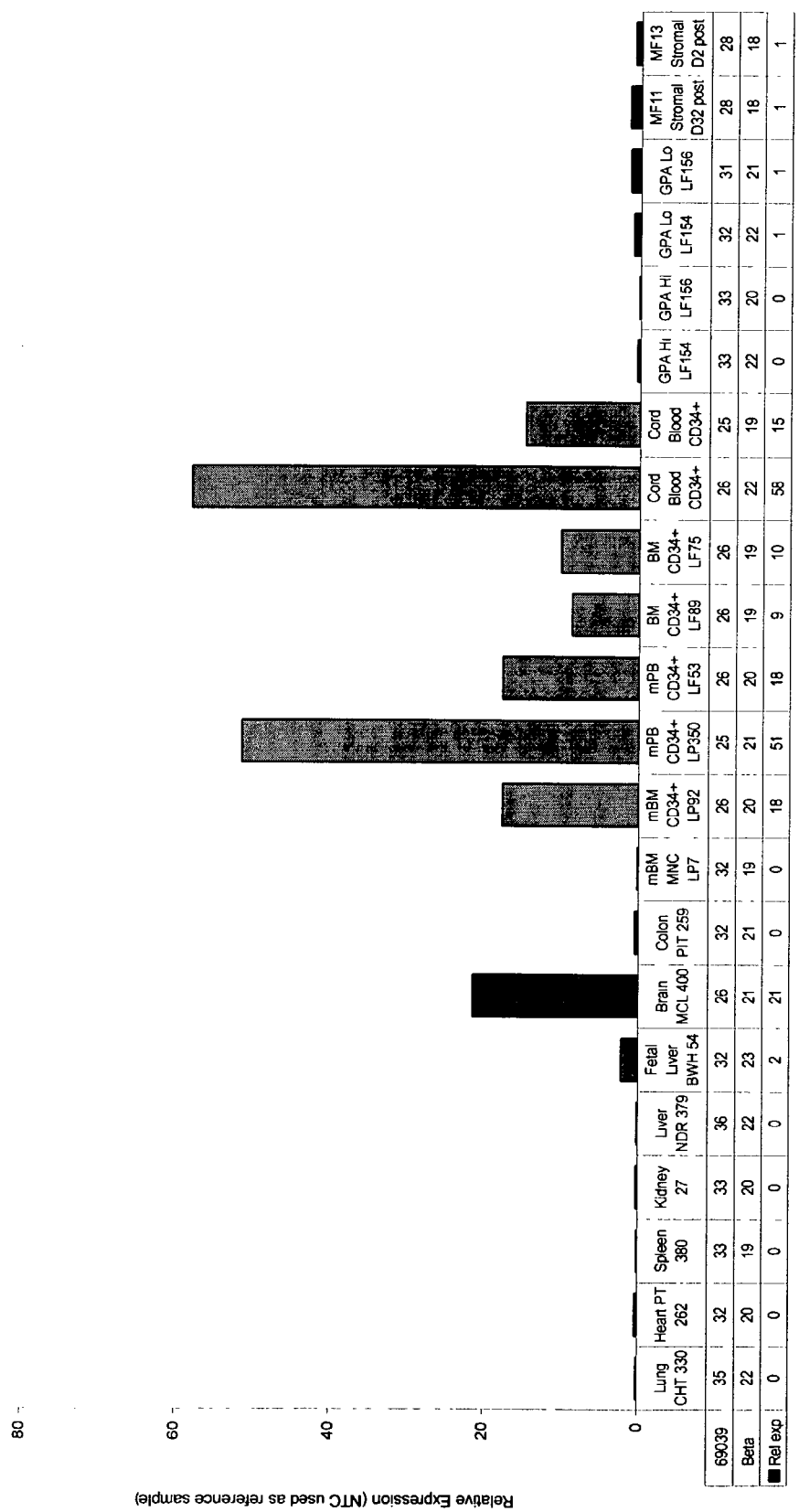
FIGS. 5A–5C are bar graphs depicting relative 69039 mRNA expression as determined by TaqMan assays on mRNA most derived from human hematological samples, e.g., bone marrow (BM), mature bone marrow (mBM), erythroid cells (Eryth), megakaryocytes (meg), neutrophils (Neut), and a negative reference sample (NTC).
Figure 5B:
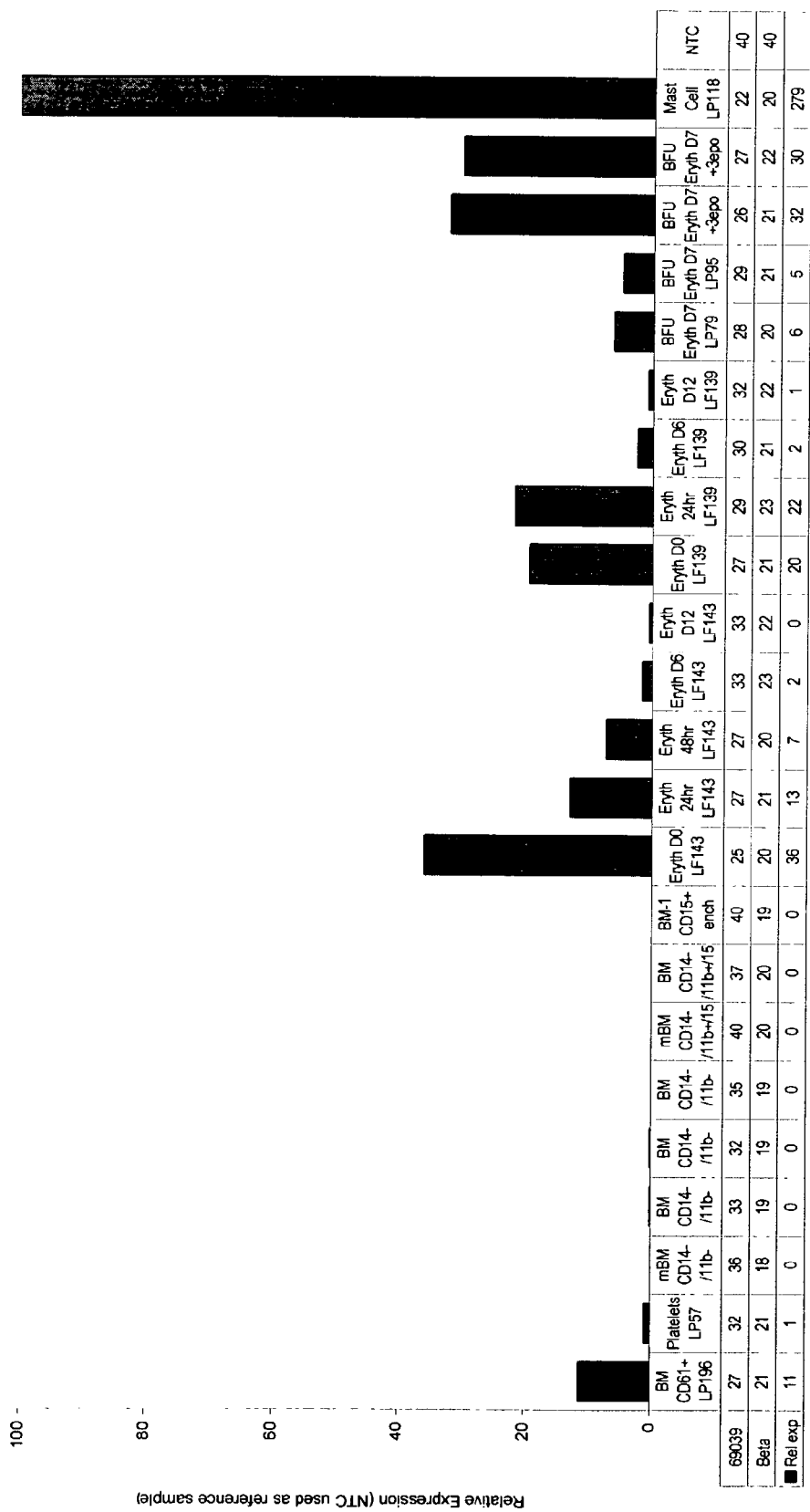
Figure 5C:
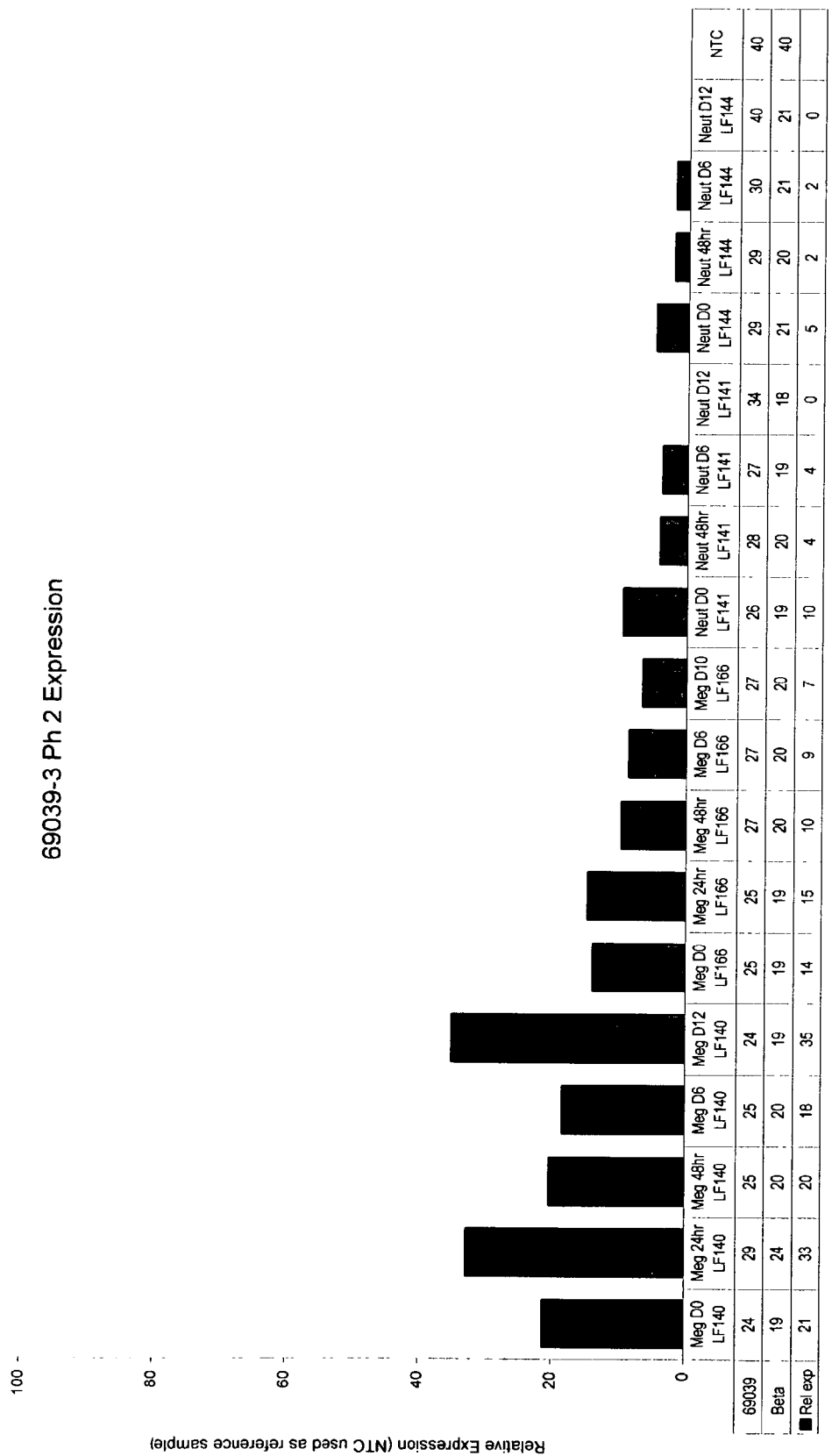

69039 mRNA is found primarily in hematopoietic progenitor CD34+ cells (FIGS. 4–5). Its expression is further enhanced in the erythroid lineage and increases as bone marrow/blood cell differentiation proceeds. More specifically, significant expression of 69039 mRNA is found in the bone marrow (BM), cord blood, mPB, and in particular, in CD34-expressing populations of cells from these tissues, such as cord blood CD34+ cells, BM CD34+ cells, and mPB CD34+ cells (FIG. 5A); as well as erythroid progenitor cells, e.g., bone marrow glycophorin A positive cells, erythropoietin treated erythroid burst forming units (BFUs), erythrocytes, in vitro generated erythroblasts, and megakaryocytes (FIGS. 5B–5C). This pattern of expression suggests a role for 69039 in the regulation of cytokine signaling during the development of cells of the erythroid lineage. In particular, data show that antagonizing the $Na^+/Ca^{2+}$ exchanger channel should increase the intracellular calcium concentration in CD34+ progenitor cells and this may assist erythroid and myeloid lineage commitment.

As used herein, a "progenitor cell" refers to any somatic cell that has the capacity to generate fully differentiated, functional progeny by differentiation and proliferation. Progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

As used herein, a "CD34-positive cell" or a "CD34-expressing cell" refers to a cell that expresses detectable levels of the CD34 antigen, preferably human CD34 antigen. The sequence for human CD34 is provided in SwissProt Accession Number P28906. The CD34 antigen is typically present on immature hematopoietic precursor cells and hematopoietic colony-forming cells in the bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)-positive B- and T-lymphoid precursors in normal bone also are CD34+. The CD34 antigen is typically present on early myeloid cells that express the CD33 antigen, but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early hematopoietic progenitor cells and decreases as the cells mature. The antigen is undetectably on fully differentiated hematopoietic cells. Approximately 60% of acute B-lymphoid leukemia's and acute myeloid leukemia express the CD34 antigen. The antigen is not expressed on chronic lymphoid leukemia (B or T lineage) or lymphomas.

As the 69039 polypeptides of the invention may modulate 69039-mediated activities, they may be useful as of for developing novel diagnostic and therapeutic agents for 69039-mediated or related disorders, e.g., blood cell-(e.g., erythroid-) associated disorders and other hematopoietic disorders.

Hematopoeitic disorders include, but are not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

As used herein, the term "erythroid associated disorders" include disorders involving aberrant (increased or deficient) erythroblast proliferation, e.g., an erythroleukemia, and aberrant (increased or deficient) erythroblast differentiation, e.g., an anemia. Erythrocyte-associated disorders include anemias such as, for example, drug-(chemotherapy-) induced anemias, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in non-hematolic disorders, for example, as a result of chemotherapy, alcoholism, or liver disease; anemia of chronic disease, such as chronic renal failure; and endocrine deficiency diseases.

Agents that modulate 69039 polypeptide or nucleic acid activity or expression can be used to treat anemias, in particular, drug-induced anemias or anemias associated with cancer chemotherapy, chronic renal failure, malignancies, adult and juvenile rheumatoid arthritis, disorders of hemoglobin synthesis, prematurity, and zidovudine treatment of HIV infection. A subject receiving the treatment can be additionally treated with a second agent, e.g., erythropoietin, to further ameliorate the condition.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, Ann. Rev. Med. 29:51 (1978); Eschbach and Adamson, Kidney Intl. 28:1 (1985). Recombinant human erythropoietin (rHuEpo or epoietin alpha) is commercially available as EPOGEN.RTM. (epoietin alpha, recombinant human erythropoietin) (Amgen Inc., Thousand Oaks, Calif.) and as PROCRIT.RTM. (epoietin alpha, recombinant human erythropoietin) (Ortho Biotech Inc., Raritan, N.J.).

Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

Aberrant expression or activity of the 69039 molecules may be involved in neoplastic disorders. Accordingly, treatment, prevention and diagnosis of cancer or neoplastic disorders related to hematopoietic cells and, in particular, cells of the erythroid lineage are also included in the present invention. Such neoplastic disorders are exemplified by erythroid leukemias, or leukemias of erythroid precursor cells, e.g., poorly differentiated acute leukemias such as erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267–97). In particular, AML can include the uncontrolled proliferation of CD34+ cells such as AML subtypes M1 and M2, myeloblastic leukemias with and without maturation, and AML subtype M6, erythroleukemia (Di Guglielmo's disease). Additional neoplastic disorders include a myelodysplastic syndrome or preleukemic disorder, e.g., oligoblastic leukemia, smoldering leukemia. Additional cancers of the erythroid lineage include erythroblastosis, and other relevant diseases of the bone marrow.

The term "leukemia" or "leukemic cancer" is intended to have its clinical meaning, namely, a neoplastic disease in which white corpuscle maturation is arrested at a primitive stage of cell development. The disease is characterized by an increased number of leukemic blast cells in the bone marrow, and by varying degrees of failure to produce normal hematopoietic cells. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukermia. In addition, leukemias with erythroid or megakaryocytic properties are considered myelogenous leukemias as well.

As highly expressed in brain, spinal cord, or dorsal root gland, 69039 may play an important role in the regulation of neural or brain disorders (e.g., pain disorders).

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

69039 mRNA is also expressed in the skin. Accordingly, modulation of 69039 activity or expression can be used to treat or prevent skin disorders. Examples of skin disorders include, but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

The 69039 protein, fragments thereof, and derivatives and other variants of the sequence in SEQ ID NO:2 thereof are collectively referred to as "polypeptides or proteins of the invention" or "69039 polypeptides or proteins". Nucleic acid molecules encoding such polypeptides or proteins are collectively referred to as "nucleic acids of the invention" or "69039 nucleic acids." 69039 molecules refer to 69039 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1 or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 69039 protein. The gene can optionally further include non-coding sequences, e.g., regulatory sequences and introns. Preferably, a gene encodes a mammalian 69039 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 69039 protein is at least 10% pure. In a preferred embodiment, the preparation of 69039 protein has less than about 30%, 20%, 10% and more preferably 5% (by dry weight), of non-69039 protein (also referred to herein as a "contaminating protein"), or of chemical precursors or non-69039 chemicals. When the 69039 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 69039 without abolishing or substantially altering a 69039 activity. Preferably the alteration does not substantially alter the 69039 activity, e.g., the activity is at least 20%, 40%, 60%, 70% or 80% of wild-type. An "essential" amino acid residue is a residue that, when altered from the wild-type sequence of 69039, results in abolishing a 69039 activity such that less than 20% of the wild-type activity is present. For example, conserved amino acid residues in 69039 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 69039 protein is preferably replaced with another amino acid residue from the same side chain family. Alternatively, in another embodiment, mutations can be introduced randomly along all or part of a 69039 coding sequence, such as by saturation mutagenesis, and the resultant mutants can be screened for 69039 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 69039 protein includes a fragment of a 69039 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 69039 molecule and a non-69039 molecule or between a first 69039 molecule and a second 69039 molecule (e.g., a dimerization interaction). Biologically active portions of a 69039 protein include peptides comprising amino acid sequences sufficiently homologous to or derived from the amino acid sequence of the 69039 protein, e.g., the amino acid sequence shown in SEQ ID NO:2, which include less amino acids than the full length 69039 proteins, and exhibit at least one activity of a 69039 protein. Typically, biologically active portions comprise a domain or motif with at least one activity of the 69039 protein, e.g., (1) transporting $Ca^{2+}$ across a membrane; (2) transporting $Na^+$ across a membrane; (3) modulating intracellular $Na^+$-dependent inactivation and $Ca^{2+}$-dependent regulation; (4) modulating (e.g., stimulate) cell differentiation, e.g., differentiation of hematopoietic cells (e.g., differentiation of blood cells (e.g., erythroid progenitor cells, such as CD34+ erythroid progenitors)); (5) modulating hematopoiesis, e.g., erythropoiesis; (6) modulating cell proliferation, e.g., proliferation of hematopoietic cells (e.g., erythroid or myeloid progenitor cells); (7) inactivating cell surface growth factor receptors, e.g., cytokine receptors; (8) modulating apoptosis, of a cell, e.g., increase apoptosis of a cancer cell, e.g., a leukemic cell, (e.g., an erythroleukemia cell); or suppress apoptosis of a blood or erythroid cell; or (9) modulating transcriptional activity, e.g., cytokine transcriptional activity. A biologically active portion of a 69039 protein can be a polypeptide that is, for example, 10, 25, 50, 100, 200 or more amino acids in length. Biologically active portions of a 69039 protein can be used as targets for developing agents which modulate a 69039 mediated activity, e.g., (1) transporting $Ca^{2+}$ across a membrane; (2) transporting Na⁺ across a membrane; (3) modulating intracellular Na⁺-dependent inactivation and Ca²⁺-dependent regulation; (4) modulating (e.g., stimulate) cell differentiation, e.g., differentiation of hematopoietic cells (e.g., differentiation of blood cells (e.g., erythroid progenitor cells, such as CD34+ erythroid progenitors)); (5) modulating hematopoiesis, e.g., erythropoiesis; (6) modulating cell proliferation, e.g., proliferation of hematopoietic cells (e.g., erythroid progenitor cells); (7) inactivating cell surface growth factor receptors, e.g., cytokine receptors; (8) modulating apoptosis, of a cell, e.g., increase apoptosis of a cancer cell, e.g., a leukemic cell, (e.g., an erythroleukemia cell); or suppress apoptosis of a blood or erythroid cell; or (9) modulating transcriptional activity, e.g., cytokine transcriptional activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403–10. BLAST nucleotide searches can be performed with the NBLAST program, score=100, wordlength=12 to obtain nucleotide sequences homologous to 69039 nucleic acid molecules of the invention. BLAST protein searches can be performed with the XBLAST program, score=50, wordlength=3 to obtain amino acid sequences homologous to 69039 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov.

Particularly preferred 69039 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity SEQ ID NO:1 or 3 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 69039 polypeptide described herein, e.g., a full-length 69039 protein or a fragment thereof, e.g., a biologically active portion of 69039 protein. Also included is a nucleic acid fragment suitable for use as a hybridization probe, which can be used, e.g., to identify a nucleic acid molecule encoding a polypeptide of the invention, 69039 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of these nucleotide sequences. In one embodiment, the nucleic acid molecule includes sequences encoding the human 69039 protein (i.e., "the coding region" of SEQ ID NO:1, as shown in SEQ ID NO:3), as well as 5' untranslated sequences. Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 110 to 257 of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3, such that it can hybridize (e.g., under a stringency condition described herein) to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

69039 Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a 69039 protein, e.g., an immunogenic or biologically active portion of a 69039 protein. A fragment can comprise those nucleotides of SEQ ID NO:1, which encode a $Na^+/Ca^{2+}$ exchanger domain of human 69039. The nucleotide sequence determined from the cloning of the 69039 gene allows for the generation of probes and primers designed for use in identifying and/or cloning other 69039 family members, or fragments thereof, as well as 69039 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 69039 nucleic acid fragment can include a sequence corresponding to a $Na^+/Ca^{2+}$ exchanger domain, one or two Calx-θ motifs.

69039 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3. Preferably, an oligonucleotide is less than about 200, 150, 120, or 100 nucleotides in length.

In one embodiment, the probe or primer is attached to a solid support, e.g., a solid support described herein.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO:2. The reverse primer can anneal to the ultimate codon, e.g., the codon immediately before the stop codon, e.g., the codon encoding amino acid residue 595 of SEQ ID NO:2. In a preferred embodiment, the annealing temperatures of the forward and reverse primers differ by no more than 5, 4, 3, or 2° C.

In a preferred embodiment the nucleic acid is a probe which is at least 10, 12, 15, 18, 20 and less than 200, more preferably less than 100, or less than 50, nucleotides in length. It should be identical, or differ by 1, or 2, or less than 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a $Na^+/Ca^{2+}$ exchanger domain from amino acids 110 to 257 of SEQ ID NO:2, and a Calx-θ motif from amino acids 385 to 485, or 519 to 594 of SEQ ID NO:2.

In another embodiment a set of primers is provided, e.g., primers suitable for use in a PCR, which can be used to amplify a selected region of a 69039 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a $Na^+/Ca^{2+}$ exchanger domain from about amino acid 110 to 257 of SEQ ID NO:2, and a Calx-θ motif from amino acids 385 to 485, or 519 to 594 of SEQ ID NO:2.

A nucleic acid fragment can encode an epitope bearing region of a polypeptide described herein.

A nucleic acid fragment encoding a "biologically active portion of a 69039 polypeptide" can be prepared by isolating a portion of the nucleotide sequence of SEQ ID NO:1 or 3, which encodes a polypeptide having a 69039 biological activity (e.g., the biological activities of the 69039 proteins are described herein), expressing the encoded portion of the 69039 protein (e.g., by recombinant expression in vitro) and assessing the activity of the encoded portion of the 69039 protein. For example, a nucleic acid fragment encoding a biologically active portion of 69039 includes a $Na^+/Ca^{2+}$ exchanger domain, e.g., amino acid residues about 110 to 257 of SEQ ID NO:2. A nucleic acid fragment encoding a biologically active portion of a 69039 polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:1, or SEQ ID NO:3.

In a preferred embodiment, a nucleic acid fragment differs by at least 1, 2, 3, 10, 20, or more nucleotides from the sequence of Genbank accession number AJ304852. Differ can include differing in length or sequence identity.

69039 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 69039 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. The encoded protein can differ by no more than 5, 4, 3, 2, or 1 amino acid. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1 or 3, e.g., as follows: by at least one but less than 10, 20, 30, or 40 nucleotides; at least one but less than 1%, 5%, 10% or 20% of the nucleotides in the subject nucleic acid. The nucleic acid can differ by no more than 5, 4, 3, 2, or 1 nucleotide. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under a stringency condition described herein, to the nucleotide sequence shown in SEQ ID NO 2 or a fragment of the sequence. Nucleic acid molecules corresponding to orthologs, homologs, and allelic variants of the 69039 cDNAs of the invention can further be isolated by mapping to the same chromosome or locus as the 69039 gene.

Preferred variants include those that are correlated with activities, such as (1) transporting $Ca^{2+}$ across a membrane; (2) transporting $Na^+$ across a membrane; (3) modulating intracellular $Na^+$-dependent inactivation and $Ca^{2+}$-dependent regulation; (4) modulating (e.g., stimulate) cell differentiation, e.g., differentiation of hematopoietic cells (e.g., differentiation of blood cells (e.g., erythroid progenitor cells, such as CD34+ erythroid progenitors)); (5) modulating hematopoiesis, e.g., erythropoiesis; (6) modulating cell proliferation, e.g., proliferation of hematopoietic cells (e.g., erythroid progenitor cells); (7) inactivating cell surface growth factor receptors, e.g., cytokine receptors; (8) modulating apoptosis, of a cell, e.g., increase apoptosis of a cancer cell, e.g., a leukemic cell, (e.g., an erythroleukemia cell); or suppress apoptosis of a blood or erythroid cell; or (9) modulating transcriptional activity, e.g., cytokine transcriptional activity.

Allelic variants of 69039, e.g., human 69039, include both functional and non-functional proteins. Functional allelic variants are naturally occurring amino acid sequence variants of the 69039 protein within a population that maintain the ability to transport $Na^+/Ca^{2+}$. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 69039, e.g., human 69039, protein within a population that do not have the ability transport $Na^+/Ca^{2+}$. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 69039 family members and, thus, which have a nucleotide sequence which differs from the 69039 sequences of SEQ ID NO:1 or SEQ ID NO:3 are intended to be within the scope of the invention.

Antisense Nucleic Acid Molecules, Ribozymes and Modified 69039 Nucleic Acid Molecules In another aspect, the invention features, an isolated nucleic acid molecule which is antisense to 69039. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 69039 coding strand, or to only a portion thereof (e.g., the coding region of human 69039 corresponding to SEQ ID NO:3). In another embodiment, the antisense nucleic acid molecule is antisense to a "noncoding region" of the coding strand of a nucleotide sequence encoding 69039 (e.g., the 5' and 3' untranslated regions).

An antisense nucleic acid can be designed such that it is complementary to the entire coding region of 69039 mRNA, but more preferably is an oligonucleotide which is antisense to only a portion of the coding or noncoding region of 69039 mRNA. For example, the antisense oligonucleotide can be complementary to the region surrounding the translation start site of 69039 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 69039 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. A ribozyme having specificity for a 69039-encoding nucleic acid can include one or more sequences complementary to the nucleotide sequence of a 69039 cDNA disclosed herein (i.e., SEQ ID NO:1 or SEQ ID NO:3), and a sequence having known catalytic sequence responsible for mRNA cleavage (see U.S. Pat. No. 5,093, 246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 69039-encoding mRNA. See, e.g., Cech et al. U.S. Pat. No. 4,987,071; and Cech et al. U.S. Pat. No. 5,116,742. Alternatively, 69039 mRNA can be used to select a catalytic RNA having a specific ribonuclease activity from a pool of RNA molecules. See, e.g., Bartel, D. and Szostak, J. W. (1993) *Science* 261:1411–1418.

69039 gene expression can be inhibited by targeting nucleotide sequences complementary to the regulatory region of the 69039 (e.g., the 69039 promoter and/or enhancers) to form triple helical structures that prevent transcription of the 69039 gene in target cells. See generally, Helene, C. (1991) *Anticancer Drug Des*. 6:569–84; Helene, C. i (1992) *Ann. N. Y. Acad. Sci*. 660:27–36; and Maher, L. J. (1992) *Bioassays* 14:807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 69039 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech*. 19:17 and Faria et al. (2001) *Nature Biotech*. 19:40–44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic &*

*Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670–675.

PNAs of 69039 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 69039 nucleic acid molecules can also be used in the analysis of single base pair mutations in a gene, (e.g., by PNA-directed PCR clamping); as 'artificial restriction enzymes' when used in combination with other enzymes, (e.g., S1 nucleases, (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 69039 nucleic acid of the invention, two complementary regions one having a fluorophore and one a quencher such that the molecular beacon is useful for quantitating the presence of the 69039 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 69039 Polypeptides

In another aspect, the invention features, an isolated 69039 protein, or fragment, e.g., a biologically active portion, for use as immunogens or antigens to raise or test (or more generally to bind) anti-69039 antibodies. 69039 protein can be isolated from cells or tissue sources using standard protein purification techniques. 69039 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 69039 polypeptide has one or more of the following characteristics:

it has the ability to transport $Ca^{2+}$ across a membrane;

it has the ability to transport $Na^+$ across a membrane;

it has the ability to modulate intracellular $Na^+$-dependent inactivation and $Ca^{2+}$-dependent regulation;

it has the ability modulate (e.g., stimulate) cell differentiation, e.g., differentiation of hematopoietic cells (e.g., differentiation of blood cells (e.g., erythroid progenitor cells, such as CD34+ erythroid progenitors));

it has the ability to modulate hematopoiesis, e.g., erythropoiesis;

it has the ability to modulate cell proliferation, e.g., proliferation of hematopoietic cells (e.g., erythroid progenitor cells);

it has the ability to inactivate cell surface growth factor receptors, e.g., cytokine receptors;

it has the ability to modulate apoptosis, of a cell, e.g., increase apoptosis of a cancer cell, e.g., a leukemic cell, (e.g., an erythroleukermia cell); or suppress apoptosis of a blood or erythroid cell;

it has the ability to modulate transcriptional activity, e.g., cytokine transcriptional activity;

it has a molecular weight, e.g., a deduced molecular weight, preferably ignoring any contribution of post translational modifications, amino acid composition or other physical characteristic of a 69039 polyeptide, e.g., the polypeptide of SEQ ID NO:2;

it has an overall sequence similarity of at least 60%, more preferably at least 70, 80, 90, or 95%, with a polypeptide a of SEQ ID NO:2; or it has a $Na^+/Ca^{2+}$ exchanger domain which is preferably about 70%, 80%, 90% or 95% with amino acid residues about 110 to 257 of SEQ ID NO:2.

In a preferred embodiment the 69039 protein, or fragment thereof, differs from the corresponding sequence in SEQ ID:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the $Na^+/Ca^{2+}$ exchanger domain (amino acids 110 to 275 of SEQ ID NO:2), or the Calx-θ motif (amino acids 385 to 485, or 519 to 594 of SEQ ID NO:2). In another preferred embodiment one or more differences are in the $Na^+/Ca^{2+}$ exchanger domain (amino acids 110 to 275 of SEQ ID NO:2), or the Calx-θ motif (amino acids 385 to 485, or 519 to 594 of SEQ ID NO:2).

Other embodiments include a protein that contain one or more changes in amino acid sequence, e.g., a change in an amino acid residue which is not essential for activity. Such 69039 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98% or more homologous to SEQ ID NO:2.

A 69039 protein or fragment is provided which varies from the sequence of SEQ ID NO:2 in regions defined by amino acids about 110 to 257 of SEQ ID NO:2 by at least one but by less than 15, 10 or 5 amino acid residues in the protein or fragment but which does not differ from SEQ ID NO:2 in regions defined by amino acids about 110 to 257 of SEQ ID NO:2. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 69039 protein includes a $Na^+/Ca^{2+}$ exchanger domain. Moreover, other biologically active portions, in which other regions of the protein are deleted, can be prepared by recombinant techniques and evaluated for one or more of the functional activities of a native 69039 protein.

In a preferred embodiment, the 69039 protein has an amino acid sequence shown in SEQ ID NO:2. In other embodiments, the 69039 protein is substantially identical to SEQ ID NO:2. In yet another embodiment, the 69039 protein is substantially identical to SEQ ID NO:2 and retains the functional activity of the protein of SEQ ID NO:2, as described in detail in the subsections above.

In a preferred embodiment, a fragment differs by at least 1, 2, 3, 10, 20, or more amino acid residues from a sequence in AJ304852.

69039 Chimeric or Fusion Proteins

In another aspect, the invention provides 69039 chimeric or fusion proteins. As used herein, a 69039 "chimeric protein" or "fusion protein" includes a 69039 polypeptide linked to a non-69039 polypeptide. A "non-69039 polypeptide" refers to a polypeptide having an amino acid sequence corresponding to a protein which is not substantially homologous to the 69039 protein, e.g., a protein which is different from the 69039 protein and which is derived from the same or a different organism. The 69039 polypeptide of the fusion protein can correspond to all or a portion e.g., a fragment described herein of a 69039 amino acid sequence. In a preferred embodiment, a 69039 fusion protein includes at least one (or two) biologically active portion of a 69039 protein. The non-69039 polypeptide can be fused to the N-terminus or C-terminus of the 69039 polypeptide.

The fusion protein can include a moiety which has a high affinity for a ligand. For example, the fusion protein can be a GST-69039 fusion protein in which the 69039 sequences are fused to the C-terminus of the GST sequences. Such fusion proteins can facilitate the purification of recombinant 69039. Alternatively, the fusion protein can be a 69039 protein containing a heterologous signal sequence at its N-terminus. In certain host cells (e.g., mammalian host cells), expression and/or secretion of 69039 can be increased through use of a heterologous signal sequence.

Fusion proteins can include all or a part of a serum protein, e.g., an IgG constant region, or human serum albumin.

The 69039 fusion proteins of the invention can be incorporated into pharmaceutical compositions and administered to a subject in vivo. The 69039 fusion proteins can be used to affect the bioavailability of a 69039 substrate. 69039 fusion proteins may be useful therapeutically for the treatment of disorders caused by, for example, (i) aberrant modification or mutation of a gene encoding a 69039 protein; (ii) mis-regulation of the 69039 gene; and (iii) aberrant post-translational modification of a 69039 protein.

Moreover, the 69039-fusion proteins of the invention can be used as immunogens to produce anti-69039 antibodies in a subject, to purify 69039 ligands and in screening assays to identify molecules which inhibit the interaction of 69039 with a 69039 substrate.

Expression vectors are commercially available that already encode a fusion moiety (e.g., a GST polypeptide). A 69039-encoding nucleic acid can be cloned into such an expression vector such that the fusion moiety is linked in-frame to the 69039 protein.

Variants of 69039 Proteins

In another aspect, the invention also features a variant of a 69039 polypeptide, e.g., which functions as an agonist (mimetics) or as an antagonist. Variants of the 69039 proteins can be generated by mutagenesis, e.g., discrete point mutation, the insertion or deletion of sequences or the truncation of a 69039 protein. An agonist of the 69039 proteins can retain substantially the same, or a subset, of the biological activities of the naturally occurring form of a 69039 protein. An antagonist of a 69039 protein can inhibit one or more of the activities of the naturally occurring form of the 69039 protein by, for example, competitively modulating a 69039-mediated activity of a 69039 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 69039 protein.

Variants of a 69039 protein can be identified by screening combinatorial libraries of mutants, e.g., truncation mutants, of a 69039 protein for agonist or antagonist activity.

Libraries of fragments e.g., N terminal, C terminal, or internal fragments, of a 69039 protein coding sequence can be used to generate a variegated population of fragments for screening and subsequent selection of variants of a 69039 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 69039 proteins. Recursive ensemble mutagenesis (REM), a new technique which enhances the frequency of functional mutants in the libraries, can be used in combination with the screening assays to identify 69039 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 69039 library. For example, a library of expression vectors can be transfected into a cell line, e.g., a cell line, which ordinarily responds to 69039 in a substrate-dependent manner. The transfected cells are then contacted with 69039 and the effect of the expression of the mutant on signaling by the 69039 substrate can be detected, e.g., binding to $Ca^{2+}$. Plasmid DNA can then be recovered from the cells which score for inhibition, or alternatively, potentiation of signaling by the 69039 substrate, and the individual clones further characterized.

In another aspect, the invention features a method of making a 69039 polypeptide, e.g., a peptide having a non-wild type activity, e.g., an antagonist, agonist, or super agonist of a naturally occurring 69039 polypeptide, e.g., a naturally occurring 69039 polypeptide. The method includes: altering the sequence of a 69039 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 69039 polypeptide a biological activity of a naturally occurring 69039 polypeptide. The method includes: altering the sequence, e.g., by substitution or deletion of one or more residues, of a 69039 polypeptide, e.g., altering the sequence of a non-conserved region, or a domain or residue described herein, and testing the altered polypeptide for the desired activity.

Anti-69039 Antibodies

In another aspect, the invention provides an anti-69039 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-69039 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 69039 polypeptide or fragment thereof. Examples of antigen-binding fragments of the anti-69039 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-69039 antibody can be a polyclonal or a monoclonal antibody. In other embodiments, the antibody can be recombinantly produced, e.g., produced by phage display or by combinatorial methods.

Phage display and combinatorial methods for generating anti-69039 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982, the contents of all of which are incorporated by reference herein).

In one embodiment, the anti-69039 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856–859; Green, L. L. et al. 1994 Nature Genet. 7:13–21; Morrison, S. L. et al. 1994 Proc. Natl. Acad. Sci. USA 81:6851–6855; Bruggeman et al. 1993 Year Immunol 7:33–40; Tuaillon et al. 1993 PNAS 90:3720–3724; Bruggeman et al. 1991 Eur J Immunol 21:1323–1326).

An anti-69039 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041–1043); Liu et al. (1987) PNAS 84:3439–3443; Liu et al., 1987, J. Immunol. 139:3521–3526; Sun et al. (1987) PNAS 84:214–218; Nishimura et al., 1987, Canc. Res. 47:999–1005; Wood et al. (1985) Nature 314:446–449; and Shaw et al., 1988, J. Natl Cancer Inst. 80:1553–1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 69039 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, Science 229:1202–1207, by Oi et al., 1986, BioTechniques 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 69039 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552–525; Verhoeyan et al. 1988 Science 239:1534; Beidler et al. 1988 J. Immunol. 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585, 089, the contents of which are hereby incorporated by reference. Other techniques for humanizing antibodies are described in Padlan et al. EP 519596 A1, published on Dec. 23, 1992.

A full-length 69039 protein or, antigenic peptide fragment of 69039 can be used as an immunogen or can be used to identify anti-69039 antibodies made with other immunogens, e.g., cells, membrane preparations, and the like. The antigenic peptide of 69039 should include at least 8 amino acid residues of the amino acid sequence shown in SEQ ID NO:2 and encompasses an epitope of 69039. Preferably, the antigenic peptide includes at least 10 amino acid residues, more preferably at least 15 amino acid residues, even more preferably at least 20 amino acid residues, and most preferably at least 30 amino acid residues.

Fragments of 69039 which include residues about 260 to 275, about 320 to 335, or about 487 to 500 can be used to make, e.g., used as immunogens or used to characterize the specificity of an antibody, antibodies against hydrophilic regions of the 69039 protein. Similarly, fragments of 69039 which include residues about 58 to 68, about 410 to 420, or about 557 to 565 can be used to make an antibody against a hydrophobic region of the 69039 protein; fragments of 69039 which include residues about 31 to 73, about 154 to 169, or about 225 to 233 can be used to make an antibody against an extracellular region of the 69039 protein; fragments of 69039 which include residues about 96 to 135, about 190 to 201, or about 252 to 595 can be used to make an antibody against an intracellular region of the 69039 protein; a fragment of 69039 which include residues about 110 to 257 of SEQ ID NO:2 (or a fragment thereof, e.g., about amino acids 110 to 150, 150 to 200, and 200 to 257 of SEQ ID NO:2) can be used to make an antibody against the $Na^+/Ca^{2+}$ exchanger domain region of the 69039 protein; a fragment of 69039 which includes residues about 385 to 485, or 519 to 594 of SEQ ID NO:2 (or a fragment thereof, e.g., about amino acids 385 to 400, 400 to 485, 519 to 550, and 550 to 592 of SEQ ID NO:2) and can be used to make an antibody against a Calx-θ motif region of the 69039 protein.

Antibodies reactive with, or specific for, any of these regions, or other regions or domains described herein are provided.

Antibodies which bind only native 69039 protein, only denatured or otherwise non-native 69039 protein, or which bind both, are with in the invention. Antibodies with linear or conformational epitopes are within the invention. Conformational epitopes can sometimes be identified by identifying antibodies that bind to native but not denatured 69039 protein.

Preferred epitopes encompassed by the antigenic peptide are regions of 69039 are located on the surface of the protein, e.g., hydrophilic regions, as well as regions with high antigenicity. For example, an Emini surface probability analysis of the human 69039 protein sequence can be used to indicate the regions that have a particularly high probability of being localized to the surface of the 69039 protein and are thus likely to constitute surface residues useful for targeting antibody production.

In a preferred embodiment the antibody can bind to the extracellular portion of the 69039 protein, e.g., it can bind to a whole cell which expresses the 69039 protein. In another embodiment, the antibody binds an intracellular portion of the 69039 protein. In preferred embodiments antibodies can bind one or more of purified antigen, membrane associated antigen, tissue, e.g., tissue sections, whole cells, preferably living cells, lysed cells, cell fractions, e.g., membrane fractions.

The anti-69039 antibody can be a single chain antibody. A single-chain antibody (scFV) may be engineered (see, for example, Colcher, D. et al. (1999) *Ann N Y Acad Sci* 880:263–80; and Reiter, Y. (1996) *Clin Cancer Res* 2:245–52). The single chain antibody can be dimerized or multimerized to generate multivalent antibodies having specificities for different epitopes of the same target 69039 protein.

In a preferred embodiment the antibody has effector function and/or can fix complement. In other embodiments the antibody does not recruit effector cells; or fix complement.

In a preferred embodiment, the antibody has reduced or no ability to bind an Fc receptor. For example, it is a isotype or subtype, fragment or other mutant, which does not support binding to an Fe receptor, e.g., it has a mutagenized or deleted Fc receptor binding region.

In a preferred embodiment, an anti-69039 antibody alters (e.g., increases or decreases) the binding of $Ca^{2+}$ of a 69039 polypeptide.

The antibody can be coupled to a toxin, e.g., a polypeptide toxin, e.g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-69039 antibody (e.g., monoclonal antibody) can be used to isolate 69039 by standard techniques, such as affinity chromatography or immunoprecipitation. Moreover, an anti-69039 antibody can be used to detect 69039 protein (e.g., in a cellular lysate or cell supernatant) in order to evaluate the abundance and pattern of expression of the protein. Anti-69039 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid which encodes an anti-69039 antibody, e.g., an anti-69039 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-69039 antibody, e.g., and antibody described herein, and method of using said cells to make a 69039 antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 69039 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 69039 proteins, mutant forms of 69039 proteins, fusion proteins, and the like).

The recombinant expression vectors of the invention can be designed for expression of 69039 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 69039 activity assays, (e.g., direct assays or competitive assays described in detail below), or to generate antibodies specific for 69039 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman, S., (1990) Gene Expression Technology: Methods in Enzymology 185, Academic Press, San Diego, Calif. 119–128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

The 69039 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA., Gossen and Bujard (1992) Proc. Natl. Acad. Sci. USA 89:5547, and Paillard (1989) Human Gene Therapy 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 69039 nucleic acid molecule within a recombinant expression vector or a 69039 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 69039 protein can be expressed in bacterial cells (such as E. coli), insect cells, yeast or mammalian cells (such as Chinese hamster ovary cells (CHO) or COS cells (African green monkey kidney cells CV-1 origin SV40 cells; Gluzman (1981) Cell123:175–182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 69039 protein. Accordingly, the invention further provides methods for producing a 69039 protein using the host cells of the invention. In one embodiment, the method includes culturing the host cell of the invention (into which a recombinant expression vector encoding a 69039 protein has been introduced) in a suitable medium such that a 69039 protein is produced. In another embodiment, the method further includes isolating a 69039 protein from the medium or the host cell.

In another aspect, the invention features, a cell or purified preparation of cells which include a 69039 transgene, or which otherwise misexpress 69039. The cell preparation can consist of human or non-human cells, e.g., rodent cells, e.g., mouse or rat cells, rabbit cells, or pig cells. In preferred embodiments, the cell or cells include a 69039 transgene, e.g., a heterologous form of a 69039, e.g., a gene derived from humans (in the case of a non-human cell). The 69039 transgene can be misexpressed, e.g., overexpressed or underexpressed. In other preferred embodiments, the cell or cells include a gene that mis-expresses an endogenous 69039, e.g., a gene the expression of which is disrupted, e.g., a knockout. Such cells can serve as a model for studying disorders that are related to mutated or mis-expressed 69039 alleles or for use in drug screening.

In another aspect, the invention features, a human cell, e.g., a hematopoietic stem cell, transformed with nucleic acid which encodes a subject 69039 polypeptide.

Also provided are cells, preferably human cells, e.g., human hematopoietic or fibroblast cells, in which an endogenous 69039 is under the control of a regulatory sequence that does not normally control the expression of the endogenous 69039 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 69039 gene. For example, an endogenous 69039 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 69039 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) Nat. Biotechnol. 14:1107; Joki et al. (2001) Nat. Biotechnol. 19:35; and U.S. Pat. No. 5,876,742. Production of 69039 polypeptide can be regulated in the subject by administering an agent (e.g., a steroid hormone) to the subject. In another preferred embodiment, the implanted recombinant cells express and secrete an antibody specific for a 69039 polypeptide. The antibody can be any antibody or any antibody derivative described herein.

Transgenic Animals

The invention provides non-human transgenic animals. Such animals are useful for studying the function and/or activity of a 69039 protein and for identifying and/or evaluating modulators of 69039 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 69039 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 69039 protein to particular cells. A transgenic founder animal can be identified based upon the presence of a 69039 transgene in its genome and/or expression of 69039 mRNA in tissues or cells of the animals. A transgenic founder animal can then be used to breed additional animals carrying the transgene. Moreover, transgenic animals carrying a transgene encoding a 69039 protein can further be bred to other transgenic animals carrying other transgenes.

69039 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 69039 protein (e.g., via a recombinant expression vector in a host cell in gene therapy applications), to detect a 69039 mRNA (e.g., in a biological sample) or a genetic alteration in a 69039 gene, and to modulate 69039 activity, as described further below. The 69039 proteins can be used to treat disorders characterized by insufficient or excessive production of a 69039 substrate or production of 69039 inhibitors. In addition, the 69039 proteins can be used to screen for naturally occurring 69039 substrates, to screen for drugs or compounds which modulate 69039 activity, as well as to treat disorders characterized by insufficient or excessive production of 69039 protein or production of 69039 protein forms which have decreased, aberrant or unwanted activity compared to 69039 wild type protein (e.g., blood cell-(e.g., erythroid-) associated disorders and other hematopoietic disorders). Moreover, the anti-69039 antibodies of the invention can be used to detect and isolate 69039 proteins, regulate the bioavailability of 69039 proteins, and modulate 69039 activity.

A method of evaluating a compound for the ability to interact with, e.g., bind, a subject 69039 polypeptide is provided. The method includes: contacting the compound with the subject 69039 polypeptide; and evaluating ability of the compound to interact with, e.g., to bind or form a complex with the subject 69039 polypeptide. This method can be performed in vitro, e.g., in a cell free system, or in vivo, e.g., in a two-hybrid interaction trap assay. This method can be used to identify naturally occurring molecules that interact with subject 69039 polypeptide. It can also be used to find natural or synthetic inhibitors of subject 69039 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 69039 proteins, have a stimulatory or inhibitory effect on, for example, 69039 expression or 69039 activity, or have a stimulatory or inhibitory effect on, for example, the expression or activity of a 69039 substrate. Compounds thus identified can be used to modulate the activity of target gene products (e.g., 69039 genes) in a therapeutic protocol, to elaborate the biological function of the target gene product, or to identify compounds that disrupt normal target gene interactions.

In one embodiment, the invention provides assays for screening candidate or test compounds that are substrates of a 69039 protein or polypeptide or a biologically active portion thereof. In another embodiment, the invention provides assays for screening candidate or test compounds that bind to or modulate an activity of a 69039 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a 69039 protein or biologically active portion thereof is contacted with a test compound, and the ability of the test compound to modulate 69039 activity is determined. Determining the ability of the test compound to modulate 69039 activity can be accomplished by monitoring, for example, transporting $Na^+/Ca^{2+}$. The cell, for example, can be of mammalian origin, e.g., human.

The ability of the test compound to modulate 69039 binding to a compound, e.g., a 69039 substrate, or to bind to 69039 can also be evaluated. This can be accomplished, for example, by coupling the compound, e.g., the substrate, with a radioisotope or enzymatic label such that binding of the compound, e.g., the substrate, to 69039 can be determined by detecting the labeled compound, e.g., substrate, in a complex. Alternatively, 69039 could be coupled with a radioisotope or enzymatic label to monitor the ability of a test compound to modulate 69039 binding to a 69039 substrate in a complex. For example, compounds (e.g., 69039 substrates) can be labeled with $^{125}I$, $^{35}S$, $^{14}C$, or $^3H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 69039 substrate) to interact with 69039 with or without the labeling of any of the interactants can be evaluated. For example, a microphysiometer can be used to detect the interaction of a compound with 69039 without the labeling of either the compound or the 69039. McConnell, H. M. et al. (1992) *Science* 257: 1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 69039.

In yet another embodiment, a cell-free assay is provided in which a 69039 protein or biologically active portion thereof is contacted with a test compound and the ability of the test compound to bind to the 69039 protein or biologically active portion thereof is evaluated. Preferred biologically active portions of the 69039 proteins to be used in assays of the present invention include fragments which participate in interactions with non-69039 molecules, e.g., fragments with high surface probability scores.

Soluble and/or membrane-bound forms of isolated proteins (e.g., 69039 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 69039 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 69039, an anti-69039 antibody or its target molecule to facilitate separation of complexed from uncomplexed forms of one or both of the proteins, as well as to accommodate automation of the assay. Binding of a test compound to a 69039 protein, or interaction of a 69039 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/69039 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 69039 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 69039 binding or activity determined using standard techniques.

Other techniques for immobilizing either a 69039 protein or a target molecule on matrices include using conjugation of biotin and streptavidin. Biotinylated 69039 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 69039 protein or target molecules but which do not interfere with binding of the 69039 protein to its target molecule. Such antibodies can be derivatized to the wells of the plate, and unbound target or 69039 protein trapped in the wells by antibody conjugation. Methods for detecting such complexes, in addition to those described above for the GST-immobilized complexes, include immunodetection of complexes using antibodies reactive with the 69039 protein or target molecule, as well as enzyme-linked assays which rely on detecting an enzymatic activity associated with the 69039 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. Current Protocols in Molecular Biology 1999, J. Wiley: New York.);

and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11: 141–8; Hage, D. S., and Tweed, S. A. (1997) *J Chromatogr B Biomed Sci Appl.* 699:499–525). Further, fluorescence energy transfer may also be conveniently utilized, as described herein, to detect binding without further purification of the complex from solution.

In a preferred embodiment, the assay includes contacting the 69039 protein or biologically active portion thereof with a known compound which binds 69039 to form an assay mixture, contacting the assay mixture with a test compound, and determining the ability of the test compound to interact with a 69039 protein, wherein determining the ability of the test compound to interact with a 69039 protein includes determining the ability of the test compound to preferentially bind to 69039 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 69039 genes herein identified. In an alternative embodiment, the invention provides methods for determining the ability of the test compound to modulate the activity of a 69039 protein through modulation of the activity of a downstream effector of a 69039 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 69039 proteins can be used as "bait proteins" in a two-hybrid assay or three-hybrid assay (see, e.g., U.S. Pat. No. 5,283,317; Zervos et al. (1993) *Cell*

72:223–232; Madura et al. (1993) *J. Biol. Chem.* 268: 12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 69039 ("69039-binding proteins" or "69039-bp") and are involved in 69039 activity. Such 69039-bps can be activators or inhibitors of signals by the 69039 proteins or 69039 targets as, for example, downstream elements of a 69039-mediated signaling pathway.

The two-hybrid system is based on the modular nature of most transcription factors, which consist of separable DNA-binding and activation domains. Briefly, the assay utilizes two different DNA constructs. In one construct, the gene that codes for a 69039 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 69039 protein can be the fused to the activator domain.) If the "bait" and the "prey" proteins are able to interact, in vivo, forming a 69039-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 69039 protein.

In another embodiment, modulators of 69039 expression are identified. For example, a cell or cell free mixture is contacted with a candidate compound and the expression of 69039 mRNA or protein evaluated relative to the level of expression of 69039 mRNA or protein in the absence of the candidate compound. When expression of 69039 mRNA or protein is greater in the presence of the candidate compound than in its absence, the candidate compound is identified as a stimulator of 69039 mRNA or protein expression. Alternatively, when expression of 69039 mRNA or protein is less (statistically significantly less) in the presence of the candidate compound than in its absence, the candidate compound is identified as an inhibitor of 69039 mRNA or protein expression. The level of 69039 mRNA or protein expression can be determined by methods described herein for detecting 69039 mRNA or protein.

In another aspect, the invention pertains to a combination of two or more of the assays described herein. For example, a modulating agent can be identified using a cell-based or a cell free assay, and the ability of the agent to modulate the activity of a 69039 protein can be confirmed in vivo, e.g., in an animal such as an animal model for blood cell-(e.g., erythroid-) associated disorders and other hematopoietic disorders This invention further pertains to novel agents identified by the above-described screening assays. Accordingly, it is within the scope of this invention to further use an agent identified as described herein (e.g., a 69039 modulating agent, an antisense 69039 nucleic acid molecule, a 69039-specific antibody, or a 69039-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 69039 with a disease; (ii) identify an individual from a minute biological sample (tissue typing); and (iii) aid in forensic identification of a biological sample. These applications are described in the subsections below.

Chromosome Mapping

The 69039 nucleotide sequences or portions thereof can be used to map the location of the 69039 genes on a chromosome. This process is called chromosome mapping. Chromosome mapping is useful in correlating the 69039 sequences with genes associated with disease.

Briefly, 69039 genes can be mapped to chromosomes by preparing PCR primers (preferably 15–25 bp in length) from the 69039 nucleotide sequences. These primers can then be used for PCR screening of somatic cell hybrids containing individual human chromosomes. Only those hybrids containing the human gene corresponding to the 69039 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 69039 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 69039 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 69039 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 69039 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 69039 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 69039 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 69039 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 69039 probes can be used to identify tissue by species and/or by organ type.

In a similar fashion, these reagents, e.g., 69039 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 69039.

Such disorders include, e.g., a disorder associated with the misexpression of 69039 gene; blood cell-(e.g., erythroid-) associated disorders and other hematopoietic disorders.

The method includes one or more of the following:

detecting, in a tissue of the subject, the presence or absence of a mutation which affects the expression of the 69039 gene, or detecting the presence or absence of a mutation in a region which controls the expression of the gene, e.g., a mutation in the 5' control region;

detecting, in a tissue of the subject, the presence or absence of a mutation which alters the structure of the 69039 gene;

detecting, in a tissue of the subject, the misexpression of the 69039 gene, at the mRNA level, e.g., detecting a non-wild type level of a mRNA;

detecting, in a tissue of the subject, the misexpression of the gene, at the protein level, e.g., detecting a non-wild type level of a 69039 polypeptide.

In preferred embodiments the method includes: ascertaining the existence of at least one of: a deletion of one or more nucleotides from the 69039 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 69039 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 69039 gene; the presence of a non-wild type splicing pattern of a messenger RNA transcript of the gene; or a non-wild type level of 69039.

Methods of the invention can be used prenatally or to determine if a subject's offspring will be at risk for a disorder.

In preferred embodiments the method includes determining the structure of a 69039 gene, an abnormal structure being indicative of risk for the disorder.

In preferred embodiments the method includes contacting a sample from the subject with an antibody to the 69039 protein or a nucleic acid, which hybridizes specifically with the gene. These and other embodiments are discussed below.

Diagnostic and Prognostic Assays

Diagnostic and prognostic assays of the invention include method for assessing the expression level of 69039 molecules and for identifying variations and mutations in the sequence of 69039 molecules.

Expression Monitoring and Profiling

The presence, level, or absence of 69039 protein or nucleic acid in a biological sample can be evaluated by obtaining a biological sample from a test subject and contacting the biological sample with a compound or an agent capable of detecting 69039 protein or nucleic acid (e.g., mRNA, genomic DNA) that encodes 69039 protein such that the presence of 69039 protein or nucleic acid is detected in the biological sample. The term "biological sample" includes tissues, cells and biological fluids isolated from a subject, as well as tissues, cells and fluids present within a subject. A preferred biological sample is serum. The level of expression of the 69039 gene can be measured in a number of ways, including, but not limited to: measuring the mRNA encoded by the 69039 genes; measuring the amount of protein encoded by the 69039 genes; or measuring the activity of the protein encoded by the 69039 genes.

The level of mRNA corresponding to the 69039 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 69039 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 69039 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 69039 genes.

The level of mRNA in a sample that is encoded by one of 69039 can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189–193), self sustained sequence replication (Guatelli et al., (1990) Proc. Natl. Acad. Sci. USA 87:1874–1878), transcriptional amplification system (Kwoh et al., (1989), Proc. Natl. Acad. Sci. USA 86:1173–1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 69039 gene being analyzed.

In another embodiment, the methods further contacting a control sample with a compound or agent capable of detecting 69039 mRNA, or genomic DNA, and comparing the presence of 69039 mRNA or genomic DNA in the control sample with the presence of 69039 mRNA or genomic DNA in the test sample. In still another embodiment, serial analysis of gene expression, as described in U.S. Pat. No. 5,695,937, is used to detect 69039 transcript levels.

A variety of methods can be used to determine the level of protein encoded by 69039. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 69039 protein in a biological sample in vitro as well as in vivo. In vitro techniques for detection of 69039 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 69039 protein include introducing into a subject a labeled anti-69039 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-69039 antibody positioned on an antibody array (as described below). The sample can be detected, e.g., with avidin coupled to a fluorescent label.

In another embodiment, the methods further include contacting the control sample with a compound or agent capable of detecting 69039 protein, and comparing the presence of 69039 protein in the control sample with the presence of 69039 protein in the test sample.

The invention also includes kits for detecting the presence of 69039 in a biological sample. For example, the kit can include a compound or agent capable of detecting 69039 protein or mRNA in a biological sample; and a standard. The compound or agent can be packaged in a suitable container. The kit can further comprise instructions for using the kit to detect 69039 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 69039 expression or activity. As used herein, the term "unwanted" includes an unwanted phenomenon involved in a biological response such as a hematopoietic disorder.

In one embodiment, a disease or disorder associated with aberrant or unwanted 69039 expression or activity is identified. A test sample is obtained from a subject and 69039 protein or nucleic acid (e.g., mRNA or genomic DNA) is evaluated, wherein the level, e.g., the presence or absence, of 69039 protein or nucleic acid is diagnostic for a subject having or at risk of developing a disease or disorder associated with aberrant or unwanted 69039 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 69039 expression or activity. For example, such methods can be used to determine whether a subject can be effectively treated with an agent for a blood cell-(e.g., erythroid-) associated disorder or another hematopoietic disorder.

In another aspect, the invention features a computer medium having a plurality of digitally encoded data records. Each data record includes a value representing the level of expression of 69039 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 69039 (e.g., other genes associated with a 69039-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 69039 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a [disordera] disorder in a subject wherein an increase in 69039 expression is an indication that the subject has or is disposed to having blood cell-(e.g., erythroid-) associated disorders and other hematopoietic disorders. The method can be used to monitor a treatment for blood cell-(e.g., erythroid-) associated disorders and other hematopoietic disorders in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 69039 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 69039 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 69039 expression.

Arrays and Uses Thereof

In another aspect, the invention features an array that includes a substrate having a plurality of addresses. At least one address of the plurality includes a capture probe that binds specifically to a 69039 molecule (e.g., a 69039 nucleic acid or a 69039 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 69039 nucleic acid, e.g., the sense or anti-sense strand. In one preferred embodiment, a subset of addresses of the plurality of addresses has a nucleic acid capture probe for 69039. Each address of the subset can include a capture probe that hybridizes to a different region of a 69039 nucleic acid. In another preferred embodiment, addresses of the subset include a capture probe for a 69039 nucleic acid. Each address of the subset is unique, overlapping, and complementary to a different variant of 69039 (e.g., an allelic variant, or all possible hypothetical variants). The array can be used to sequence 69039 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 69039 polypeptide or fragment thereof. The polypeptide can be a naturally-occurring interaction partner of 69039 polypeptide. Preferably, the polypeptide is an antibody, e.g., an antibody described herein (see "Anti-69039 Antibodies," above), such as a monoclonal antibody or a single-chain antibody.

In another aspect, the invention features a method of analyzing the expression of 69039. The method includes providing an array as described above; contacting the array with a sample and detecting binding of a 69039-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 69039. If a sufficient number of diverse samples is analyzed, clustering (e.g., hierarchical clustering, k-means clustering, Bayesian clustering and the like) can be used to identify other genes which are co-regulated with 69039. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 69039 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 69039-associated disease or disorder; and processes, such as a cellular transformation associated with a 69039-associated disease or disorder. The method can also evaluate the treatment and/or progression of a 69039-associated disease or disorder The array is also useful for ascertaining differential expression patterns of one or more genes in normal and abnormal cells. This provides a battery of genes (e.g., including 69039) that could serve as a molecular target for diagnosis or therapeutic intervention.

In another aspect, the invention features an array having a plurality of addresses. Each address of the plurality includes a unique polypeptide. At least one address of the plurality has disposed thereon a 69039 polypeptide or fragment thereof. Methods of producing polypeptide arrays are described in the art, e.g., in De Wildt et al. (2000). *Nature Biotech*. 18, 989–994; Lueking et al. (1999). *Anal. Biochem*. 270, 103–111; Ge, H. (2000). *Nucleic Acids Res*. 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80,85, 90, 95 or 99% identical to a 69039 polypeptide or fragment thereof. For example, multiple variants of a 69039 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 69039 binding compound, e.g., an antibody in a sample from a subject with specificity for a 69039 polypeptide or the presence of a 69039-binding protein or ligand.

The array is also useful for ascertaining the effect of the expression of a gene on the expression of other genes in the same cell or in different cells (e.g., ascertaining the effect of 69039 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 69039 or from a cell or subject in which a 69039 mediated response has been elicited, e.g., by contact of the cell with 69039 nucleic acid or protein, or administration to the cell or subject 69039 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 69039 (or does not express as highly as in the case of the 69039 positive plurality of capture probes) or from a cell or subject which in which a 69039 mediated response has not been elicited (or has been elicited to a lesser extent than in the first sample); contacting the array with one or more inquiry probes (which is preferably other than a 69039 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 69039 or from a cell or subject in which a 69039-mediated response has been elicited, e.g., by contact of the cell with 69039 nucleic acid or protein, or administration to the cell or subject 69039 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 69039 (or does not express as highly as in the case of the 69039 positive plurality of capture probes) or from a cell or subject in which a 69039 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 69039, e.g., analyzing structure, function, or relatedness to other nucleic acid or amino acid sequences. The method includes: providing a 69039 nucleic acid or amino acid sequence; comparing the 69039 sequence with one or more preferably a plurality of sequences from a collection of sequences, e.g., a nucleic acid or protein sequence database; to thereby analyze 69039.

Detection of Variations or Mutations

The methods of the invention can also be used to detect genetic alterations in a 69039 gene, thereby determining if a subject with the altered gene is at risk for a disorder characterized by misregulation in 69039 protein activity or nucleic acid expression, such as blood cell-(e.g., erythroid-) associated disorders and other hematopoietic disorders. In preferred embodiments, the methods include detecting, in a sample from the subject, the presence or absence of a genetic alteration characterized by at least one of an alteration affecting the integrity of a gene encoding a 69039-protein, or the mis-expression of the 69039 gene. For example, such genetic alterations can be detected by ascertaining the existence of at least one of 1) a deletion of one or more nucleotides from a 69039 gene; 2) an addition of one or more nucleotides to a 69039 gene; 3) a substitution of one or more nucleotides of a 69039 gene, 4) a chromosomal rearrangement of a 69039 gene; 5) an alteration in the level of a messenger RNA transcript of a 69039 gene, 6) aberrant modification of a 69039 gene, such as of the methylation pattern of the genomic DNA, 7) the presence of a non-wild type splicing pattern of a messenger RNA transcript of a 69039 gene, 8) a non-wild type level of a 69039-protein, 9) allelic loss of a 69039 gene, and 10) inappropriate post-translational modification of a 69039-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 69039-gene. This method can include the steps of collecting a sample of cells from a subject, isolating nucleic acid (e.g., genomic, mRNA or both) from the sample, contacting the nucleic acid sample with one or more primers which specifically hybridize to a 69039 gene under conditions such that hybridization and amplification of the 69039-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 69039 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 69039 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 69039 nucleic acid or a putative variant (e.g., allelic variant) thereof. A probe can have one or more mismatches to a region of a 69039 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 69039 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 69039 gene and detect mutations by comparing the sequence of the sample 69039 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 69039 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 69039 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 69039 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control 69039 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6: 1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 69039 nucleic acid.

In a preferred embodiment the set includes a first and a second oligonucleotide. The first and second oligonucleotide can hybridize to the same or to different locations of SEQ ID NO:1 or the complement of SEQ ID NO:1. Different locations can be different but overlapping, or non-overlapping on the same strand. The first and second oligonucleotide can hybridize to sites on the same or on different strands.

The set can be useful, e.g., for identifying SNP's, or identifying specific alleles of 69039. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 69039 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 69039 gene.

Use of 69039 Molecules as Surrogate Markers

The 69039 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 69039 molecules of the invention may be detected, and may be correlated with one or more biological states in vivo. For example, the 69039 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 69039 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 69039 marker) transcription or expression, the amplified marker may be in a quantity which is more readily detectable than the drug itself. Also, the marker may be more easily detected due to the nature of the marker itself; for example, using the methods described herein, anti-69039 antibodies may be employed in an immune-based detection system for a 69039 protein marker, or 69039-specific radiolabeled probes may be used to detect a 69039 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The 69039 molecules of the invention are also useful as pharmacogenomic markers. As used herein, a "pharmacogenomic marker" is an objective biochemical marker that correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 69039 protein or RNA) for specific tumor markers in a subject, a drug or course of treatment may be selected that is optimized for the treatment of the specific tumor likely to be present in the subject. Similarly, the presence or absence of a specific sequence mutation in 69039 DNA may correlate 69039 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-69039 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 69039 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 69039 molecules of the present invention or 69039 modulators according to that individual's drug response genotype. Pharmacogenormics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 69039 expression or activity, by administering to the subject a 69039 or an agent which modulates 69039 expression or at least one 69039 activity. Subjects at risk for a disease which is caused or contributed to by aberrant or unwanted 69039 expression or activity can be identified by, for example, any or a combination of diagnostic or prognostic assays as described herein. Administration of a prophylactic agent can occur prior to the manifestation of symptoms characteristic of the 69039 aberrance, such that a disease or disorder is prevented or, alternatively, delayed in its progression. Depending on the type of 69039 aberrance, for example, a 69039, 69039 agonist or 69039 antagonist agent can be used for treating the subject. The appropriate agent can be determined based on screening assays described herein.

It is possible that some 69039 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 69039 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 69039 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 69039 expression is through the use of aptamer molecules specific for 69039 protein. Aptamers are nucleic acid molecules having a tertiary structure which permits them to specifically bind to protein ligands (see, e.g., Osborne, et al. (1997) *Curr. Opin. Chem Biol.* 1: 5–9; and Patel, D. J. (1997) *Curr Opin Chem Biol* 1:32–46). Since nucleic acid molecules may in many cases be more conveniently introduced into target cells than therapeutic protein molecules may be, aptamers offer a method by which 69039 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 69039 disorders. For a description of antibodies, see the Antibody section above.

In circumstances wherein injection of an animal or a human subject with a 69039 protein or epitope for stimulating antibody production is harmful to the subject, it is possible to generate an immune response against 69039 through the use of anti-idiotypic antibodies (see, for example, Herlyn, D. (1999) *Ann Med* 31:66–78; and Bhattacharya-Chatterjee, M., and Foon, K. A. (1998) *Cancer Treat Res.* 94:51–68). If an anti-idiotypic antibody is introduced into a mammal or human subject, it should stimulate the production of anti-anti-idiotypic antibodies, which should be specific to the 69039 protein. Vaccines directed to a disease characterized by 69039 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 69039 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 69039 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of 69039 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating 69039 expression or activity for therapeutic purposes. Accordingly, in an exemplary embodiment, the modulatory method of the invention involves contacting a cell with a 69039 or agent that modulates one or more of the activities of 69039 protein activity associated with the cell. An agent that modulates 69039 protein activity can be an agent as described herein, such as a nucleic acid or a protein, a naturally-occurring target molecule of a 69039 protein (e.g., a 69039 substrate or receptor), a 69039 antibody, a 69039 agonist or antagonist, a peptidomimetic of a 69039 agonist or antagonist, or other small molecule.

In one embodiment, the agent stimulates one or 69039 activities. Examples of such stimulatory agents include active 69039 protein and a nucleic acid molecule encoding 69039. In another embodiment, the agent inhibits one or more 69039 activities. Examples of such inhibitory agents include antisense 69039 nucleic acid molecules, anti-69039 antibodies, and 69039 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 69039 protein or nucleic acid molecule. In one embodiment, the method involves administering an agent (e.g., an agent identified by a screening assay described herein), or combination of agents that modulates (e.g., up regulates or down regulates) 69039 expression or activity. In another embodiment, the method involves administering a 69039 protein or nucleic acid molecule as therapy to compensate for reduced, aberrant, or unwanted 69039 expression or activity.

Stimulation of 69039 activity is desirable in situations in which 69039 is abnormally downregulated and/or in which increased 69039 activity is likely to have a beneficial effect. For example, stimulation of 69039 activity is desirable in situations in which a 69039 is downregulated and/or in which increased 69039 activity is likely to have a beneficial effect. Likewise, inhibition of 69039 activity is desirable in situations in which 69039 is abnormally upregulated and/or in which decreased 69039 activity is likely to have a beneficial effect.

Pharmacogenomics

The 69039 molecules of the present invention, as well as agents, or modulators which have a stimulatory or inhibitory effect on 69039 activity (e.g., 69039 gene expression) as identified by a screening assay described herein can be administered to individuals to treat (prophylactically or therapeutically) 69039 associated disorders (e.g., blood cell- (e.g., erythroid-) associated disorders and other hematopoietic disorders) associated with aberrant or unwanted 69039 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 69039 molecule or 69039 modulator as well as tailoring the dosage and/or therapeutic regimen of treatment with a 69039 molecule or 69039 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 69039 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 69039 molecule or 69039 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 69039 molecule or 69039 modulator, such as a modulator identified by one of the exemplary screening assays described herein.

The present invention further provides methods for identifying new agents, or combinations, that are based on identifying agents that modulate the activity of one or more of the gene products encoded by one or more of the 69039 genes of the present invention, wherein these products may be associated with resistance of the cells to a therapeutic agent. Specifically, the activity of the proteins encoded by the 69039 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 69039 protein can be applied in clinical trials. For example, the effectiveness of an agent determined by a screening assay as described herein to increase 69039 gene expression, protein levels, or upregulate 69039 activity, can be monitored in clinical trials of subjects exhibiting decreased 69039 gene expression, protein levels, or downregulated 69039 activity. Alternatively, the effectiveness of an agent determined by a screening assay to decrease 69039 gene expression, protein levels, or downregulate 69039 activity, can be monitored in clinical trials of subjects exhibiting increased 69039 gene expression, protein levels, or upregulated 69039 activity. In such clinical trials, the expression or activity of a 69039 gene, and preferably, other genes that have been implicated in, for example, a 69039-associated disorder can be used as a "read out" or markers of the phenotype of a particular cell.

69039 Informatics

The sequence of a 69039 molecule is provided in a variety of media to facilitate use thereof. A sequence can be provided as a manufacture, other than an isolated nucleic acid or amino acid molecule, which contains a 69039. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 69039 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 69039, e.g., analyzing structure, function, or relatedness to one or more other nucleic acid or amino acid sequences. The method includes: providing a 69039 nucleic acid or amino acid sequence; comparing the 69039 sequence with a second sequence, e.g., one or more preferably a plurality of sequences from a collection of sequences, e.g., a nucleic acid or protein sequence database to thereby analyze 69039. The method can be performed in a machine, e.g., a computer, or manually by a skilled artisan.

The method can include evaluating the sequence identity between a 69039 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 69039 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 69039 sequence, or record, in machine-readable form; comparing a second sequence to the 69039 sequence; thereby analyzing a sequence. Comparison can include comparing to sequences for sequence identity or determining if one sequence is included within the other, e.g., determining if the 69039 sequence includes a sequence being compared. In a preferred embodiment the 69039 or second sequence is stored on a first computer, e.g., at a first site and the comparison is performed, read, or recorded on a second computer, e.g., at a second site. E.g., the 69039 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 69039-associated disease or disorder or a pre-disposition to a 69039-associated disease or disorder, wherein the method comprises the steps of determining 69039 sequence information associated with the subject and based on the 69039 sequence information, determining whether the subject has a 69039-associated disease or disorder or a pre-disposition to a 69039-associated disease or disorder and/or recommending a particular treatment for the disease, disorder or pre-disease condition.

The invention further provides in an electronic system and/or in a network, a method for determining whether a subject has a 69039-associated disease or disorder or a pre-disposition to a disease associated with a 69039 wherein the method comprises the steps of determining 69039 sequence information associated with the subject, and based on the 69039 sequence information, determining whether the subject has a 69039-associated disease or disorder or a pre-disposition to a 69039-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 69039 sequence of the subject to the 69039 sequences in the database to thereby determine whether the subject as a 69039-associated disease or disorder, or a pre-disposition for such.

The present invention also provides in a network, a method for determining whether a subject has a 69039 associated disease or disorder or a pre-disposition to a 69039-associated disease or disorder associated with 69039, said method comprising the steps of receiving 69039 sequence information from the subject and/or information related thereto, receiving phenotypic information associated with the subject, acquiring information from the network corresponding to 69039 and/or corresponding to a 69039-associated disease or disorder (e.g., blood cell-(e.g., erythroid-) associated disorders and other hematopoietic disorders), and based on one or more of the phenotypic information, the 69039 information (e.g., sequence information and/or information related thereto), and the acquired information, determining whether the subject has a 69039-associated disease or disorder or a pre-disposition to a 69039-associated disease or disorder. The method may further comprise the step of recommending a particular treatment for the disease, disorder or pre-disease condition.

The present invention also provides a method for determining whether a subject has a 69039 -associated disease or disorder or a pre-disposition to a 69039-associated disease or disorder, said method comprising the steps of receiving information related to 69039 (e.g., sequence information and/or information related thereto), receiving phenotypic information associated with the subject, acquiring information from the network related to 69039 and/or related to a 69039-associated disease or disorder, and based on one or more of the phenotypic information, the 69039 information, and the acquired information, determining whether the subject has a 69039-associated disease or disorder or a pre-disposition to a 69039-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Example 1

Identification and Characterization of Human 69039 cDNA

The human 69039 nucleic acid sequence is recited as follows:

```
CCAGTTTGGGAGACAGGACTTGAAGGCTATTGCTGCATTTCCATCCCCAGTATTCCCAGC   (SEQ ID NO:1)

TATTTCAAGCCATTTTTCAACGGAGTCTCCACCAGATGGTTTGGAGGACAGAGCAGCTAT

TTGTGCCTCCCATTGACATCTATTTTTCCAAGTGAGAGACTGCCCCATATGTTAGTGCAA

TATGTCACTGGAGGTGAAGCATCAGTTGTATTGGTGGGAACCTGCGGTTTGCTGTCCCCT

TTTTCCTCATGCCTTTTCCTGCCTCTCTGATCTTTTCTAGGTCTCTGGCCTATCAGGAGG

ACAACTGGTGCTGCAATAGAAGCCAGTGGCTAAGTCTCGTGTATGGCGTGGTTAAGGTTG

CAGCCTCTCACCTCTGCCTTCCTCCATTTTGGGCTGGTTACCTTTGTGCTCTTCCTGAAT

GGTCTTCGAGCAGAGGCTGGTGGCTCAGGGGACGTGCCAAGCACAGGGCAGAACAATGAG

TCCTGTTCAGGGTCATCGGACTGCAAGGAGGGTGTCATCCTGCCAATCTGGTACCCGGAG
```

-continued

```
AACCCTTCCCTTGGGGACAAGATTGCCAGGGTCATTGTCTATTTTGTGGCCCTGATATAC
ATGTTCCTTGGGGTGTCCATCATTGCTGACCGCTTCATGGCATCTATTGAAGTCATCACC
TCTCAAGAGAGGGAGGTGACAATTAAGAAACCCAATGGAGAAACCAGCACAACCACTATT
CGGGTCTGGAATGAAACTGTCTCCAACCTGACCCTTATGGCCCTGGGTTCCTCTGCTCCT
GAGATACTCCTCTCTTTAATTGAGGTGTGTGGTCATGGGTTCATTGCTGGTGATCTGGGA
CCTTCTACCATTGTAGGGAGTGCAGCCTTCAACATGTTCATCATCATTGGCATCTGTGTC
TACGTGATCCCAGACGGAGAGACTCGCAAGATCAAGCATCTACGAGTCTTCTTCATCACC
GCTGCTTGGAGTATCTTTGCCTACATCTGGCTCTATATGATTCTGGCAGTCTTCTCCCCT
GGTGTGGTCCAGGTTTGGGAAGGCCTCCTCACTCTCTTCTTCTTTCCAGTGTGTGTCCTT
CTGGCCTGGGTGGCAGATAAACGACTGCTCTTCTACAAATACATGCACAAAAAGTACCGC
ACAGACAAACACCGAGGAATTATCATAGAGACAGAGGGTGACCACCCTAAGGGCATTGAG
ATGGATGGGAAAATGATGAATTCCCATTTTCTAGATGGGAACCTGGTGCCCCTGGAAGGG
AAGGAAGTGGATGAGTCCCGCAGAGAGATGATCCGGATTCTCAAGGATCTGAAGCAAAAA
CACCCAGAGAAGGACTTAGATCAGCTGGTGGAGATGGCCAATTACTATGCTCTTTCCCAC
CAACAGAAGAGCCGCGCCTTCTACCGTATCCAAGCCACTCGTATGATGACTGGTGCAGGC
AATATCCTGAAGAAACATGCAGCAGAACAAGCCAAGAAGGCCTCCAGCATGAGCGAGGTG
CACACCGATGAGCCTGAGGACTTTATTTCCAAGGTCTTCTTTGACCCATGTTCTTACCAG
TGCCTGGAGAACTGTGGGGCTGTACTCCTGACAGTGGTGAGGAAAGGGGGAGACATGTCA
AAGACCATGTATGTGGACTACAAAACAGAGGATGGTTCTGCCAATGCAGGGGCTGACTAT
GAGTTCACAGAGGGCACGGTGGTTCTGAAGCCAGGAGAGACCCAGAAGGAGTTCTCCGTG
GGCATAATTGATGACGACATTTTTGAGGAGGATGAACACTTCTTTGTAAGGTTGAGCAAT
GTCCGCATAGAGGAGGAGCAGCCAGAGGAGGGGATGCCTCCAGCAATATTCAACAGTCTT
CCCTTGCCTCGGGCTGTCCTAGCCTCCCCTTGTGTGGCCACAGTTACCATCTTGGATGAT
GACCATGCAGGCATCTTCACTTTTGAATGTGATACTATTCATGTCAGTGAGAGTATTGGT
GTTATGGAGGTCAAGGTTCTGCGGACATCAGGTGCCCGGGGTACAGTCATCGTCCCCTTT
AGGACAGTAGAAGGGACAGCCAAGGGTGGCGGTGAGGACTTTGAAGACACATATGGGGAG
TTGGAATTCAAGAATGATGAAACTGTGTAAGTAACCTTCCTGTATTCTGCCCCTCCCTGA
CCCCATCTTTTGCCATCTCTTTCTGTCTTTCTGTACTGCACTTTACAACATTTCCTTGTG
TTTGTGTTAATGTCAAACTTTGGTTCCATCACAGGTATGCAGGATCAGCAGACACCACTG
GACAGGTTCTGCTTCCAAACTCTTCTTCAGTTTTCTCACTTTAAATTGTTTCTGGGCAAG
GAATCCTGTGACAAGAGCTAAGGACACAAAACATTTTCTTCTCTGAAACACAAAATGATA
GCTGGTGGAGCTGTGGGATGACAGAAGTTTTGTGATATCAGATTTTGGAGAATTCTTGTG
ACTAAGAAGGACTAGAGAACTGCTTGGGCCTCTTCTTCCTCCCTTCCTCATATGAAGGGT
ATCTATGAGCTTTG.
```

The human 69039 sequence (FIG. 1; SEQ ID NO:1), which is approximately 2534 nucleotides long. The nucleic acid sequence includes an initiation codon (ATG) and a termination codon (TAA) which are underscored above. The region between and inclusive of the initiation codon and the termination codon is a methionine-initiated coding sequence of about 1788 nucleotides, including the termination codon (nucleotides indicated as "coding" of SEQ ID NO:1; SEQ ID NO:3). The coding sequence encodes a 595 amino acid protein (SEQ ID NO:2), which is recited as follows:

```
MAWLRLQPLTSAFLHFGLVTFVLFLNGLRAEAGGSGDVPSTGQNNESC          (SEQ ID NO:2)
SGSSDCKEGVIL
PIWYPENPSLGDKIARVIVYFVALIYMFLGVSIIADRFMASIEVTTSQEREVTIKKPNGE
TSTTTIRVWNETVSNLTLMALGSSAPEILLSLIEVCGHGFIAGDLGPSTIVGSAAFNMFI
IIGICVYVIPDGETRKIKHLRVFFITAAWSIFAYIWLYMILAVFSPGVVQVWEGLLTLFF
FPVCVLLAWVADKRLLFYKYMHKKYRTDKHRGIIIETEGDHPKGIEMDGKMMNSHFLDGN
LVPLEGKEVDESRREMIRILKDLKQKHPEKDLDQLVEMANYYALSHQQKSRAFYRIQATR
MMTGAGNILKKHAAEQAKKASSMSEVHTDEPEDFISKVFFDPCSYQCLENCGAVLLTVVR
KGGDMSKTMYVDYKTEDGSANAGADYEFTEGTVVLKPGETQKEFSVGIIDDDIFEEDEHF
FVRLSNVRIEEEQPEEGMPPAIFNSLPLPRAVLASPCVATVTILDDDHAGIFTFECDTIH
VSESIGVMEVKVLRTSGARGTVIVPFRTVEGTAKGGGEDFEDTYGELEFKNDETV.
```

Example 2

Tissue Distribution of 69039 mRNA by TaqMan Analysis

Endogenous human 69039 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 69039 in various human tissues a primer/probe set was designed. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Table 2. Down regulated 69039 mRNA was detected in myeloid and erythroid cells (Tables 3–5).

TABLE 2

| Tissue Type | Mean | B 2 Mean | ∂∂ Ct | Expression |
|---|---|---|---|---|
| Artery normal | 36 | 22 | 13 | 0 |
| Aorta diseased | 39 | 23 | 16 | 0 |
| Vein normal | 35 | 20 | 15 | 0 |
| Coronary SMC | 36 | 21 | 15 | 0 |
| HUVEC | 31 | 21 | 10 | 1 |
| Hemangioma | 33 | 20 | 13 | 0 |
| Heart normal | 34 | 21 | 13 | 0 |

TABLE 2-continued

| Tissue Type | Mean | B 2 Mean | ∂∂ Ct | Expression |
|---|---|---|---|---|
| Heart CHF | 36 | 21 | 15 | 0 |
| Kidney | 32 | 21 | 12 | 0 |
| Skeletal Muscle | 26 | 22 | 4 | 64 |
| Adipose normal | 34 | 20 | 14 | 0 |
| Pancreas | 36 | 22 | 13 | 0 |
| primary osteoblasts | 34 | 20 | 14 | 0 |
| Bladder | 33 | 21 | 13 | 0 |
| Skin normal | 29 | 22 | 8 | 5 |
| Spinal cord normal | 30 | 21 | 9 | 2 |
| Brain Cortex normal | 26 | 22 | 4 | 54 |
| Brain Hypothalamus normal | 29 | 23 | 7 | 10 |
| Nerve | 31 | 22 | 10 | 1 |
| DRG (Dorsal Root Ganglion) | 29 | 22 | 8 | 4 |
| Breast normal | 35 | 21 | 14 | 0 |
| Breast tumor | 36 | 21 | 15 | 0 |
| Ovary normal | 34 | 20 | 14 | 0 |
| Ovary Tumor | 36 | 19 | 17 | 0 |
| Prostate BPH | 31 | 20 | 11 | 0 |
| Prostate Tumor | 33 | 21 | 12 | 0 |
| Salivary glands | 35 | 21 | 14 | 0 |
| Colon normal | 33 | 20 | 13 | 0 |
| Colon Tumor | 32 | 22 | 10 | 1 |
| Lung normal | 31 | 18 | 13 | 0 |
| Lung tumor | 33 | 21 | 12 | 0 |
| Lung COPD | 31 | 19 | 12 | 0 |
| Colon IBD | 33 | 19 | 15 | 0 |
| Liver normal | 37 | 21 | 16 | 0 |
| Liver fibrosis | 35 | 21 | 14 | 0 |
| Spleen normal | 34 | 19 | 15 | 0 |
| Tonsil normal | 31 | 19 | 12 | 0 |
| Lymph node normal | 34 | 21 | 13 | 0 |
| Small intestine normal | 34 | 21 | 13 | 0 |
| Macrophages | 33 | 17 | 16 | 0 |
| Synovium | 36 | 19 | 17 | 0 |
| BM-MNC | 34 | 19 | 16 | 0 |
| Activated PBMC | 32 | 18 | 14 | 0 |
| Neutrophils | 36 | 18 | 18 | 0 |
| Megakaryocytes | 26 | 19 | 7 | 8 |
| Erythroid | 31 | 20 | 11 | 0 |
| positive control | 29 | 21 | 8 | 5 |

TABLE 3

| | 69039Beta | | | Rel exp | | | |
|---|---|---|---|---|---|---|---|
| Lung CHT 330 | 35.08 | 21.52 | 35 | 22 | 14 | 14 | 0 |
| Heart PT 262 | 31.81 | 20.01 | 32 | 20 | 12 | 12 | 0 |
| Spleen 380 | 33.02 | 18.79 | 33 | 19 | 14 | 14 | 0 |
| Kidney 27 | 32.52 | 20.01 | 33 | 20 | 13 | 13 | 0 |

TABLE 3-continued

|  |  |  | 69039Beta |  | Rel exp |  |  |
|---|---|---|---|---|---|---|---|
| Liver NDR 379 | 35.94 | 22.27 | 36 | 22 | 14 | 14 | 0 |
| Fetal Liver BWH 54 | 32.19 | 23.29 | 32 | 23 | 9 | 9 | 2 |
| Brain MCL 400 | 26.31 | 20.76 | 26 | 21 | 6 | 6 | 21 |
| Colon PIT 259 | 32.22 | 21.01 | 32 | 21 | 11 | 11 | 0 |
| mBM MNC LP7 | 31.77 | 18.54 | 32 | 19 | 13 | 13 | 0 |
| mBM CD34 + LP92 | 26.09 | 20.26 | 26 | 20 | 6 | 6 | 18 |
| mPB CD34 + LP350 | 25.14 | 20.86 | 25 | 21 | 4 | 4 | 51 |
| mPB CD34 + LF53 | 26.02 | 20.19 | 26 | 20 | 6 | 6 | 18 |
| BM CD34 + LF89 | 25.73 | 18.87 | 26 | 19 | 7 | 7 | 9 |
| BM CD34 + LF75 | 25.84 | 19.2 | 26 | 19 | 7 | 7 | 10 |
| Cord Blood CD34 + MF1 | 25.9 | 21.79 | 26 | 22 | 4 | 4 | 58 |
| Cord Blood CD34 + LF101 | 25.14 | 19.05 | 25 | 19 | 6 | 6 | 15 |
| GPA Hi LF154 | 33.43 | 21.8 | 33 | 22 | 12 | 12 | 0 |
| GPA Hi LF156 | 33.3 | 20.23 | 33 | 20 | 13 | 13 | 0 |
| GPA Lo LF154 | 32.15 | 21.87 | 32 | 22 | 10 | 10 | 1 |
| GPA Lo LF156 | 30.82 | 21.15 | 31 | 21 | 10 | 10 | 1 |
| MF11 Stromal D32 post irrad | 28.04 | 18.46 | 28 | 18 | 10 | 10 | 1 |
| MF13 Stromal D2 post irrad | 28.06 | 17.56 | 28 | 18 | 11 | 11 | 1 |

TABLE 4

|  |  |  | 69039-Beta |  | Rel exp |  |  |
|---|---|---|---|---|---|---|---|
| BM CD61 + LP196 | 27.22 | 20.73 | 27 | 21 | 6 | 6 | 11 |
| Platelets LP57 | 31.6 | 21.35 | 32 | 21 | 10 | 10 | 1 |
| mBM CD14-/11b-/15 + LF120 | 36.15 | 18.36 | 36 | 18 | 18 | 18 | 0 |
| BM CD14-/11b-/15 + LF54 | 32.83 | 19.3 | 33 | 19 | 14 | 14 | 0 |
| BM CD14-/11b-/15 + LF128 | 31.93 | 18.5 | 32 | 19 | 13 | 13 | 2 |
| BM CD14-/11b-/15 + LF145 | 35.11 | 19.29 | 35 | 19 | 16 | 16 | 0 |
| mBM CD14-/11b + /15 + LF120 | 40 | 19.91 | 40 | 20 | 20 | 20 | 0 |
| BM CD14-/11b + /15 + LF106 | 36.79 | 19.55 | 37 | 20 | 17 | 17 | 0 |
| BM-1 CD15 + ench LP41 | 40 | 19.39 | 40 | 19 | 21 | 21 | 0 |
| Eryth D0 LF143 | 25.1 | 20.3 | 25 | 20 | 5 | 5 | 36 |
| Eryth 24 hr LF143 | 26.94 | 20.65 | 27 | 21 | 6 | 6 | 13 |
| Eryth 48 hr LF143 | 27.28 | 20.17 | 27 | 20 | 7 | 7 | 7 |
| Eryth D6 LF143 | 32.85 | 23.47 | 33 | 23 | 9 | 9 | 2 |
| Eryth D12 LF143 | 33.45 | 22.38 | 33 | 22 | 11 | 11 | 0 |
| Eryth D0 LF139 | 27.08 | 21.4 | 27 | 21 | 6 | 6 | 20 |
| Eryth 24 hr LF139 | 28.59 | 23.07 | 29 | 23 | 6 | 6 | 22 |
| Eryth D6 LF139 | 30.18 | 21.47 | 30 | 21 | 9 | 9 | 2 |
| Eryth D12 LF139 | 31.98 | 21.71 | 32 | 22 | 10 | 10 | 1 |
| BFU Eryth D7 LP79 | 27.77 | 20.44 | 28 | 20 | 7 | 7 | 6 |
| BFU Eryth D7 LP95 | 28.89 | 21.21 | 29 | 21 | 8 | 8 | 5 |
| BFU Eryth D7 + 3epo LP81 | 26.22 | 21.27 | 26 | 21 | 5 | 5 | 32 |
| BFU Eryth D7 + 3epo LP104 | 26.64 | 21.59 | 27 | 22 | 5 | 5 | 30 |
| Mast Cell LP118 | 21.92 | 20.08 | 22 | 20 | 2 | 2 | 279 |

TABLE 5

|  |  |  | 69039Beta |  | Rel exp |  |  |
|---|---|---|---|---|---|---|---|
| Meg D0 LF140 | 24.13 | 18.58 | 24 | 19 | 6 | 6 | 21 |
| Meg 24 hr LF140 | 29.21 | 24.28 | 29 | 24 | 5 | 5 | 33 |
| Meg 48 hr LF140 | 25.27 | 19.65 | 25 | 20 | 6 | 6 | 20 |
| Meg D6 LF140 | 25.34 | 19.58 | 25 | 20 | 6 | 6 | 18 |
| Meg D12 LF140 | 24.21 | 19.38 | 24 | 19 | 5 | 5 | 35 |
| Meg D0 LF166 | 25.34 | 19.17 | 25 | 19 | 6 | 6 | 14 |
| Meg 24 hr LF166 | 25.38 | 19.29 | 25 | 19 | 6 | 6 | 15 |
| Meg 48 hr LF166 | 26.84 | 20.16 | 27 | 20 | 7 | 7 | 10 |
| Meg D6 LF166 | 26.64 | 19.79 | 27 | 20 | 7 | 7 | 9 |
| Meg D10 LF166 | 27.17 | 19.92 | 27 | 20 | 7 | 7 | 7 |
| Neut D0 LF141 | 26.12 | 19.42 | 26 | 19 | 7 | 7 | 10 |
| Neut 48 hr LF141 | 27.93 | 19.99 | 28 | 20 | 8 | 8 | 4 |
| Neut D6 LF141 | 27.21 | 19.14 | 27 | 19 | 8 | 8 | 4 |
| Neut D12 LF141 | 34.12 | 18.17 | 34 | 18 | 16 | 16 | 0 |
| Neut D0 LF144 | 28.99 | 21.26 | 29 | 21 | 8 | 8 | 5 |
| Neut 48 hr LF144 | 29.03 | 20.04 | 29 | 20 | 9 | 9 | 2 |
| Neut D6 LF144 | 29.73 | 20.62 | 30 | 21 | 9 | 9 | 2 |
| Neut D12 LF144 | 40 | 20.63 | 40 | 21 | 19 | 19 | 0 |
| NTC | 40 | 40 | 40 | 40 | 0 | 0 |  |

Example 3

Tissue Distribution of 69039 mRNA by Northern Analysis

Northern blot hybridizations with various RNA samples can be performed under standard conditions and washed under stringent conditions, i.e., 0.2×SSC at 65° C. A DNA probe corresponding to all or a portion of the 69039 cDNA (SEQ ID NO:1) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 4

Recombinant Expression of 69039 in Bacterial Cells

In this example, 69039 is expressed as a recombinant glutathione-S-transferase (GST) fusion polypeptide in *E. coli* and the fusion polypeptide is isolated and characterized. Specifically, 69039 is fused to GST and this fusion polypeptide is expressed in *E. coli*, e.g., strain PEB199. Expression of the GST-69039 fusion protein in PEB 199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 69039 Protein in COS Cells

To express the 69039 gene in COS cells (e.g., COS-7 cells, CV-1 origin SV40 cells; Gluzman (1981) *Cell* 123: 175–182), the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 69039 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 69039 DNA sequence is amplified by PCR using two primers. The 5' primer contains the restriction site of interest followed by approximately twenty nucleotides of the 69039 coding sequence starting from the initiation codon; the 3' end sequence contains complementary sequences to the other restriction site of interest, a translation stop codon, the HA tag or FLAG tag and the last 20 nucleotides of the 69039 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 69039 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 69039-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed., Cold Spring Harbor Laboratory*, Cold Spring Harbor Laboratory Press, Cold Spring Harbor, N.Y. The expression of the 69039 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 69039 coding sequence is cloned directly into the polylinker of the pCDNA/Amp vector using the appropriate restriction sites. The resulting plasmid is transfected into COS cells in the manner described above, and the expression of the 69039 polypeptide is detected by radiolabelling and immunoprecipitation using a 69039 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a candidate compound capable of modulating hematopoiesis, comprising:
   i) combining a compound to be tested with a sample comprising a polypeptide selected from the group consisting of:
      a) a polypeptide comprising an amino acid sequence which is at least 95% identical to the amino acid sequence of SEQ ID NO:2, wherein the polypeptide has $Na^+/Ca^{2+}$ exchanger activity; and
      b) a polypeptide which is encoded by a nucleic acid molecule comprising a nucleotide sequence which is at least 95% identical to SEQ ID NO:1 or SEQ ID NO:3, wherein the polypeptide has $Na^+/Ca^{2+}$ exchanger activity;
   under conditions suitable for binding of the test compound to the polypeptide;
   ii) detecting binding of the test compound to the polypeptide to thereby identify a compound which binds to the polypeptide;
   iii) combining the compound selected in part ii) with hematopoietic cells expressing the polypeptide; and
   iv) determining the effect of the compound on the proliferation/differentiation of the hematopoietic cells;
thereby identifying a compound capable of modulating hematopoiesis.

2. The method of claim 1, wherein the sample is selected from the group consisting of an isolated polypeptide, a membrane-bound form of the polypeptide or a cell expressing the polypeptide.

3. The method of claim 1, wherein the compound is a small molecule.

4. The method of claim 1, wherein the polypeptide further comprises heterologous sequences.

5. The method of claim 1, wherein the binding of the test compound to the polypeptide is detected by a method selected from the group consisting of:
   a) a competition binding assay;
   b) an immunoassay; and
   c) a yeast two-hybrid assay.

6. The method of claim 1, wherein the binding of the test compound to the polypeptide is detected is by an assay for an activity of the polypeptide.

7. The method of claim 6, wherein the assay for activity is selected from the group consisting of:
   i) transport of sodium across a membrane; and
   ii) transport of calcium across a membrane.

8. A method for identifying a candidate compound capable of modulating hematopoiesis, comprising:
   i) combining a compound to be tested with a sample comprising a polypeptide selected from the group consisting of:
      a) a polypeptide comprising the amino acid sequence of SEQ ID NO:2; and
      b) a polypeptide encoded by the nucleotide sequence set forth in SEQ ID NO:1 or SEQ ID NO:3;

under conditions suitable for binding of the test compound to the polypeptide;

ii) detecting binding of the test compound to the polypeptide to thereby identify a compound which binds to the polypeptide;

iii) combining the compound selected in part ii) with hematopoietic cells expressing the polypeptide; and iv) determining the effect of the compound on the proliferation/differentiation of the hematopoietic cells;

thereby identifying a compound capable of modulating hematopoiesis.

9. The method of claim 8, wherein the sample is selected from the group consisting of an isolated polypeptide, a membrane-bound form of the polypeptide or a cell expressing the polypeptide.

10. The method of claim 8, wherein the compound is a small molecule.

11. The method of claim 8, wherein the polypeptide further comprises heterologous sequences.

12. The method of claim 8, wherein the binding of the test compound to the polypeptide is detected by a method selected from the group consisting of:
   a) a competition binding assay;
   b) an immunoassay; and
   c) a yeast two-hybrid assay.

13. The method of claim 8, wherein the binding of the test compound to the polypeptide is detected is by an assay for an activity of the polypeptide.

14. The method of claim 13, wherein the assay for activity is selected from the group consisting of:
   i) transport of sodium across a membrane; and
   ii) transport of calcium across a membrane.

* * * * *